US008173359B2

(12) United States Patent
Ponce et al.

(10) Patent No.: US 8,173,359 B2
(45) Date of Patent: *May 8, 2012

(54) METHODS AND APPARATUS AND ASSAYS OF BACTERIAL SPORES

(75) Inventors: Adrian Ponce, Altadena, CA (US); Gregory H. Bearman, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 83 days.

This patent is subject to a terminal disclaimer.

(21) Appl. No.: 11/810,005

(22) Filed: Jun. 4, 2007

(65) Prior Publication Data

US 2008/0113384 A1 May 15, 2008

Related U.S. Application Data

(63) Continuation of application No. 10/355,462, filed on Jan. 31, 2003, now abandoned.

(60) Provisional application No. 60/353,268, filed on Feb. 1, 2002, provisional application No. 60/395,372, filed on Jul. 12, 2002, provisional application No. 60/414,170, filed on Sep. 27, 2002.

(51) Int. Cl.

*C12Q 1/00* (2006.01)
*C12Q 1/06* (2006.01)
*G01N 33/20* (2006.01)

(52) U.S. Cl. .................................. 435/4; 435/39; 436/82

(58) Field of Classification Search ........................ None
See application file for complete search history.

(56) References Cited

U.S. PATENT DOCUMENTS

| | | | | |
|---|---|---|---|---|
| 4,560,665 | A | 12/1985 | Nakae et al. | 436/172 |
| 4,943,522 | A | 7/1990 | Eisinger et al. | |
| 4,965,211 | A | 10/1990 | Wieder et al. | 436/543 |
| 5,124,268 | A | 6/1992 | Dakubu | 436/547 |
| 5,792,330 | A | 8/1998 | Petersen et al. | 204/452 |
| 5,830,769 | A | 11/1998 | Wieder et al. | 436/536 |
| 5,876,960 | A | 3/1999 | Rosen | 435/39 |
| 6,136,549 | A | 10/2000 | Feistel | 435/7.1 |
| 6,242,268 | B1 | 6/2001 | Wieder et al. | 436/538 |
| 6,569,630 | B1 | 5/2003 | Vivekananda et al. | 435/6 |
| 6,599,715 | B1 | 7/2003 | Vanderberg et al. | 435/34 |
| 6,766,817 | B2 | 7/2004 | da Silva | |
| 6,918,404 | B2 | 7/2005 | da Silva | |
| 7,066,586 | B2 | 6/2006 | da Silva | |
| 7,306,930 | B2 | 12/2007 | Ponce et al. | 435/34 |
| 7,608,419 | B2 | 10/2009 | Ponce | |
| 7,611,862 | B2 | 11/2009 | Ponce | |
| 2002/0018203 | A1* | 2/2002 | Battle et al. | 356/319 |
| 2002/0135772 | A1 | 9/2002 | Bornhop et al. | 356/450 |
| 2003/0064427 | A1 | 4/2003 | Felkner et al. | 435/31 |
| 2003/0138876 | A1 | 7/2003 | Ponce et al. | 435/34 |
| 2004/0014154 | A1 | 1/2004 | Ponce et al. | 435/7.32 |
| 2005/0136508 | A1 | 6/2005 | Ponce | 435/39 |
| 2006/0292664 | A1 | 12/2006 | Ponce | 435/34 |
| 2007/0031916 | A1 | 2/2007 | Ponce | 435/34 |
| 2007/0117175 | A1 | 5/2007 | Ponce | 435/29 |

FOREIGN PATENT DOCUMENTS

| | | | |
|---|---|---|---|
| EP | 0283289 | | 9/1988 |
| JP | 063843/1989 | | 3/1989 |
| JP | 501494/1997 | | 2/1997 |
| WO | 87/07955 | | 12/1987 |
| WO | 95/04280 | | 2/1995 |
| WO | 00/63422 | | 10/2000 |
| WO | 01/83561 | A2 | 11/2001 |
| WO | 03/024491 | A2 | 3/2003 |
| WO | 03/065009 | A2 | 8/2003 |
| WO | 03/067211 | A3 | 8/2003 |

OTHER PUBLICATIONS

Canada et al. Binding of Terbium and Cisplatin to C13 Human Ovarian Cencer Cells Using Time-Resolved Terbium Luminescence; Biochimica et Biophysica Acta, vol. 1448 (1998) pp. 85-98.*

Kozuka et al. Ultrastructural Localization of Dipicolinic Acid in Dormant Spores of *Bacillus subtilis* by Immunoelectron Microscopy With Colloidal Gold Particles; Journal of Bacteriology, vol. 162, No. 3 (1985) pp. 1250-1254.*

Zaitoun et al. Chelating Behavior Between Metal Ions and EDTA in Sol-Gel Matrix; Journal of Physical Chemistry B, vol. 101 (1997) p. 1857-1860.*

PCT International Search Report for PCT/US2006/022988 filed on Jun. 13, 2006 in the name of California Institute of Technology.

(Continued)

*Primary Examiner* — Rebecca Prouty
*Assistant Examiner* — Paul Martin
(74) *Attorney, Agent, or Firm* — Steinfl & Bruno, LLP

(57) ABSTRACT

A sample of unknown bacterial spores is added to a test strip. The sample of unknown bacterial spores is drawn to a first sample region on the test strip by capillary action. Species-specific antibodies are bound to the sample when the unknown bacterial spores match the species-specific antibodies, otherwise the sample is left unbound. DPA is released from the bacterial spores in the bound sample. The terbium ions are combined with the DPA to form a Tb-DPA complex. The combined terbium ions and DPA are excited to generate a luminescence characteristic of the combined terbium ions and DPA to detect the bacterial spores. A live/dead assay is performed by a release of the DPA for live spores and a release of DPA for all spores. The detection concentrations are compared to determine the fraction of live spores. Lifetime-gated measurements of bacterial spores to eliminate any fluorescence background from organic chromophores comprise labeling the bacterial spore contents with a long-lifetime lumophore and detecting the luminescence after a waiting period. Unattended monitoring of bacterial spores in the air comprises the steps of collecting bacterial spores carried in the air and repeatedly performing the Tb-DPA detection steps above. The invention is also apparatus for performing the various methods disclosed above.

10 Claims, 10 Drawing Sheets

OTHER PUBLICATIONS

PCT Written Opinion for PCT/US2006/022988 filed on Jun. 13, 2006 in the name of California Institute of Technology, et al.

A. J. Alvarez, M. Khanna, G A. Toranzos, and G Stotzky, "Amplification of DNA bound on clay minerals," *Molecular Ecology*, vol. 7, pp. 775-778, 1998.

R. I. Amann, W. Ludwig, and K. H. Schleifer, "Phylogenetic Identification and in-Situ Detection of Individual Microbial-Cells without Cultivation," *Microbiological Reviews*, vol. 59,pp. 143-169, 1995.

Balzani V, Decola L, Prodi L, Scandola F: Photochemistry of Supramolecular Species. *Pure Appl Chem* 1990, 62:1457-1466.

Balzani V: Supramolecular Photochemistry. *Pure Appl Chem* 1990, 62:1099-1102.

D. L. Balkwill, F. R. Leach, J. T. Wilson, J. F. McNabb, and D. C. White, "Equivalence of Microbial Biomass Measures Based on Membrane Lipid and Cell-Wall Components, Adenosine-Triphosphate, and Direct Counts in Subsurface Aquifer Sediments," *Microbial Ecology*, vol. 16, pp. 73-84, 1988.

P. Belgrader. W. Benett, D. Hadley. I. Richards, P. Station, R. Mariella and F. P. Milanovich, "Infectious disease-PCR detection of bacteria in seven minutes." *Science*, vol. 284. pp. 449-450, 1999.

C.I. Elkin. S.B, Brown. S.N. Nasarabadi, R.G. Langlois, F.P. Milanovich, B.W. Colston, and G.D. Marshall. "A reusable flow-through polymerase chain reaction instrument for the continuous monitoring of infectious biological agents," *Analyt. Chem*. vol. 75, pp. 3446-3450, 2003.

M. Carl. R. Hawkins, N. Coulson. I. Lowe. D.L. Robertson. W.M. Nelson, R.W. Titball and J.N. Woody. "Detection of spores of *Bacillus-anthracis* using the polymerase chain-reaction," *J. Infectious Diseases*, vol. 165, pp. 1145-1148. 1992.

A. Castro and R.T. Okinaka, "Ultrasensitive, direct detection of a specific DNA sequence of *Bacillus anthracis* in solution," *Analyst*. vol. 125. pp. 9-11, 1999.

B. D. Church and H. Halvorson, "Dependence of the Heat Resistance of Bacterial Endospores on Their Dipicolinic acid Content," *Nature*, vol. 183, pp. 124-125, 1959.

R. Connally, D. Veal, and J. Piper, "High resolution detection of fluorescently labeled microorganisms in environmental samples using time-resolved fluorescence microscopy," *Fems Microbiology Ecology*, vol. 41, pp. 239-245, 2002.

Enserink M: ANTHRAX: Biodefence Hampered by Inadequate Tests. *Science* 2001, 294:1266-1267.

J.W. Ezzell. T.G. Absbire. S.F. Little, B.C. Lidgerding. and C. Brown, "Identification of *Bacillus-anthracis* by using monoclonal-antibody to cell-wall antibody to cell-wall galacttose-N-acetylglucosamine polysaccharide," *J. Clin. MIcrobiol*, vol. 28. pp. 223-231, 1990.

Grenthe I: Stability Relationships among the Rare Earth Dipicolinates. *Journal of the American Chemical Society* 1961, 83: 360-364.

W.D. Griffiths and G.A.L. Decosemo. "The assessment of bioaerosols-A critical- review," *J. Aerosol Sci.*. vol. 25, pp. 1425-1458. 1994.

W.D. Griffiths, I.W. Stewan. S.J. Futter, S.L. Upton, and D. Mark, "The development of sampling methods for the assessment of indoor bioaerosols," *J. Aerosol ScL*, vol. 28. pp. 437-457, 1997.

I. Henderson. C.J. Duggleby, and P.C.B. Turnbull. "Differentiation of *Bacillus-anthracis* from other *Bacillus-cereus* group bacteria with the PCR," *Int. J. Systematic Bacteriol.*, vol. 44. pp. 99-105. 1994.

J. Ho, "Future of biological aerosol detection," *Analyrica Chimica Acta*, vol. 457, pp. 125-148, 2002.

G. Horneck, H. Bucker, and G. Reitz, "Long-Term Survival of Bacterial-Spores in-Space," *Life Sciences and Space Research*), vol. 14, pp. 41-45, 1994.

W. D. Horrocks Jr., "Lanthanide Ion Luminescence in Coordination Chemistry and Biochemistry," in *Progress in Inorganic Chemistry*, vol. 31. New York: Wiley, 1984, pp. 1.

Hunnicutt, D. W., M. J. Kempf, and M. J. McBride. 2002. Mutations in *Flavobacteriumjohnsoniae gldF*and *gldG* disrupt gliding motility and interfere with membrane localization of GldA. *J. Bacteriol*. 184: 2370-2378.

T.V. Inglesby, D.A. Henderson, J.G. Bartlett, M.S. Ascher. E. Eitzen, A.M. Friedlander, J. Hauer. J. McDade, M.T. OSterholm, T. O'Toole. G. Parker, T.M.mPerl, P.K. Russel, and K. Tonat, "Anthrax as a biological weapon-Medical and public health management," *JAMA*, vol. 281, pp. 1735-1745. 1999.

K. Ito, K. Nakagawa, S. Murakami, H. Arakawa, and M. Maeda, "Highly sensitive simultaneous Bioluminescent measurement of acetate kinase and pyruvate phosphate dikinase activities using a firefly luciferase-luciferin reaction and its application to a tandem Bioluminescent enzyme immunoassay," *Analytical Sciences*, vol 19, pp. 105-109, 2003.

F.W. Janssen, A.J. Lund. and L.E. Anderson, "Colorimetric assay for dipicolinic acid In bacterial spores," *Science*, vol. 127. pp. 26-27, 1958.

M. Johns. L. Harrington, R.W. Titball, and D.L. Leslie. "Improved methods for the detection of *Bacillus-anthracis* spores by the polymerase chain-reaction," *Lett. Appl. Microbiol*. vol. 18, pp. 236-238.1994.

J. G Jones, "Effect of Environmental-Factors on Estimated Viable and Total Populations of Planktonic Bacteria in Lakes and Experimental Enclosures," *Freshwater Biology*, vol. 7, pp. 67-91, 1977.

Kempf. M. J. and M. J. McBride. 2000. Transposon insertions in the *Flavobacterium johnsoniae ftsX* gene disrupt gliding motility and cell division. J. *Bacteriol*.182: 1671-1679.

J. Knight, "US postal service puts anthrax detectors to the test," *Nature*, vol. 417, pp. 579-579, 2002.

L. J. Kricka, "Chemiluminescence and bioluminescence," *Analytical Chemistry*, vol. 71, pp. 305R-308R, 1999.

D.B. Lacy and R.J. Collier. "Structure and function of anthrax toxin," in *Anthrax, Current Topics* In *Microbiology and Immunology*, vol. 271, pp. 61-85, 2002.

D. Lawrence, S. Heitefuss, and H.S.H. Seifert, "Differentiation of *Bacillus-anthracis* from *bacillus-cereus* by gas-chromatographic whole-cell fatty-acid analysis," *J.* Clin. *Microbiol*. vol. 29, pp. 1S08-1512, 1991.

Lehn JM: Supramolecular Chemistry-Scope and Perspectives Molecules, Supermolecules, and Molecular Devices. *Angewandte Chemie-International Edition in English 1998*, 27:89-112.

Lester E et al: "A second-generation anthrax smoke detector" IEEE Engineering in Medicine and Biology Magazine, IEEE Service Center, Pisacataway, NJ, US, vol. 23, No. 1, Jan. 2004, pp. 130-135, XP001201545 ISSN: 0739-5175 the whole document.

N. A. Logan, J.A. Carman, I. Melling, and R.C.W. Berkeley. "Identification of *Bacillus-antbracis* by api tesIS," *J. Medical Microbial*. vol. 20. pp. 75-85, 1985.

A. Lundin,"Use of firefly luciferase in ATP-related assays of biomass, enzymes, and metabolites," *Bioluminescence and Chemiluminescence, PtC*, vol. 305, pp. 346-370,2000.

R. L. Mancinelli and M. Klovstad, "Martian soil and UV radiation: microbial viability assessment on spacedraft surfaces," *Planetary and Space Science*, vol. 48, pp. 1093-1097, 2000.

G Manfredi, A. Spinazzola, N. Checcarelli, and A. Naini, "Assay of mitochondrial ATP synthesis in animal cells," *Methods in Cell Biology*. vol. 65, vol. 65, pp. 133-145, 2001.

McBride, M. J. And M. J. Kempf. 1996. Development of techniques for the genetic manipulation of the gliding bacterium *Cytophaga johnsonae*. J. *Bacteriol*. 178: 583-590.

A. C. Mitchell, J. E. Wall, J. G. Murray, and C.G. Morgan, "Direct modulation of the effective sensitivity of a CCD detector: a new approach to time-resolved fluorescence imaging," *Journal of Microscopy-Oxford*, vol. 206, pp. 225-232, 2002.

M. M. Moeseneder, J. M. Arrieta, G Muyzer, C. Winter, and G J. Herndl, "Optimization of terminal-restriction fragment length polymorphism analysis for complex marine bacterioplankton communities and comparison with denaturing gradient gel electrophoresis," *Applied and Environmental Microbiology*, vol. 65, pp. 3518-3525, 1999.

C. G Morgan and A. C. Mitchell, "Fluorescence lifetime imaging: An emerging technique in fluorescence microscopy," *Chromosome Research*, vol. 4, pp. 261-263, 1996.

W. Nicholson and P. Setlow; "Sporulation, germination and outgrowth," *Molecular biology methods for bacillus*, S. Cutting, Ed. Sussex, England: John Wiley and Sons, 1990, 391-450).

M. Paidhungat, B. Setlow, A. Driks, and P. Setlow, "Characterization of spores of *Bacillus subtilis* which lack dipicolinic acid," *Journal ofBacteriology*, vol. 182, pp. 5505-5512, 2000.
G. Patra, P. Sylvestre, V. Ramisse, I. Therasse, and IL. Guesdon. "Isolation of a specific chromosomic DNA sequence of *Bacillus anthracis* and its possible use in diagnosis," *Fems Immunol. Medical Microbiol.*, vol. 15. pp. 223-231, 1996.
A.P. Phillips, K.L. Martin, N. L. Cross, and R.G. Drake, "Evaluation of immunoradiometric and Elisa versions of a microtitre plate assay for *Bacillusanlhracis* spores," *J. Immunological Merhod1*, vol. 70, pp. 75-81, 1984.
A.P. Phillips and K.L. Martin. "Quantitative immunofluorescenoe studies of the serology of *bacillus-anthracis* spores," *Appl. Environmental Microbiol.*, vol. 46, pp. 1430-1432, 1983.
V. Ramisse, G. Patra. H. Garrigue. J.L. Guesdon, and M. Mock, "Identification and characterization of *Bacillus anthracis* by multiplex PCR analysis of sequences on plasmids pXO1 and pX02 and chromosomal DNA," Ferns *Microbiol. Lett.* vol. 145, pp. 9-16, 1996.
C. Redmond, M.J. Pearce, R.T. Manchee, and B.P. Berdal, "Deadly relic of the great war," *Nature*. vol. 393. pp. 747-748, 1998.
Rosen DL, Sharpless C, McGown LB: Bacterial Spore Detection and Determination by Use of Terbium Dipicolinate Photoluminescence. *Anal Chem* 1997, 69: 1082-1085.
Rosen DL: Wavelength Pair Selection for Bacterial Endospore Detection by Use of Terbium Dipicolinate Photoluminescence. *Appl Optics* 1998, 37: 805-807.
Sabbatini N, Guardigli M, Lehn J M: Luminescent Lanthanide Complexes as Photochemical Supramolecular Devices. *Coord Chem Rev 1993*, vol. 123:201-228.
M. Schena, D. Shalon, R. W. Davis, and P. O. Brown, "Quantitative Monitoring of Gene-Expression Patterns with a Complementary-DNA Microarray," *Science*, vol. 270, pp. 467470, 1995.
L. Brewer: *Systematics and the Properties of the Lanthanides*. Edited by Sinha S: NATO ASI Series 109; 1983.
P. Sneath, "Longevity of micro-organisms," *Nature*, vol. 195, pp. 643-646, 1962.
P.J. Stopa, "The flow cytometry of *Bacillus anthracis* spores revisited," *Cytometry*, vol. 41, pp. 237-244, 2000.
B.N. Strizhkov, A.L. Drobyshev, V.M. Mikhailovlch, and A.D. Mirzabekov, "PCR amplification on a microarray of gel-immobilized oligonucleotides: Detection of bacterial toxin- and drug-resistant genes and their mutations," *Biotechnique.*, vol. 29. pp. 844-??? 2000.
V. Torsvik, I. Goksoyr, and F. L. Daae, "High Diversity in DNA of Soil Bacteria," *Applied and Environmental Microbiology*, vol. 56, pp. 782-787, 1990.
P.C.B. Turnbull. "Definitive identification of *Bacillus anthsacis-A* review," *J. Applied Microbiol*, vol. 87. pp. 237-240. 1999.
M. Varughese, A.V. Teixeira, S.H. Liu. and S.H. Leppla. "Identification of a receptor-binding region within domain 4 of the protective antigen component of anthrax *toxin." Infection and Immunity*, vol. 67, pp. 1860-1865, 1999.
Venkateswaran, K., M. Kempf. F. Chen, M. Satomi, W. Nicholson, and R. Kern. 2003. *Bacillus nealsonii* sp. nov. isolated from a spacecraft assembly facility, whose spores are gamma-radiation resistant. *Int. J. Syst. Evol. Microbiol*. 53: 165-172.
G Vereb, E. Jares-Erijman, P. R. Selvin, and T. M. Jovin, "Temporally and spectrally resolved imaging microscopy oflanthanide chelates," *Biophysical Journal*, vol. 74, pp. 2210-2222, 1998.
R. H. Vreeland, W. D. Rosenzweig, and D. W. Powers, "Isolation of a 250 million-year old halotolerant bacterium from a primary salt crystal," *Nature*, vol. 407, pp. 897-900,2000.
D. C. White, W. M. Davis, J. S. Nickels, J. D. King, and R. J. Bobbie, "Determination of the Sedimentary Microbial Biomass by Extractable Lipid Phosphate," *Oecologia*, vol. 40, pp. 51-62, 1979.
U.S. Appl. No. 10/987,202, filed Nov. 12, 2004, Ponce.
Beeby, A., et al. , "Luminescence imaging microscopy and lifetime mapping using kinetically stable lanthanide (III) complexes", *Journal of Photochemistry and Photobiology*, B: Biology 57, pp. 83-89 (2000).
Belgrader, et al., "A minisonicator to rapidly disrupt bacterial spores for DNA analysis", Analytical Chemistry, 71, pp. 4232-4236 (1999).
Beverly, M.B., et al., "Analysis of Dipicolinic Acid in Bacterial Spores by Electron Monochromator-Mass Spectrometry," *Presented at the 47th ASMS Conference on Mass Spectrometry and Allied Topics*, Dallas, Texas, 2 pages total (Jun. 13-17, 1999).
Biothreat Alert (BTA™) (2001) anonymous.
Branda, S., et al., "Fruiting body formation by *Bacillus subtilis*," *PNAS*, vol. 98, No. 20, 11621-11626 (Sep. 25, 2001).
Elbanowski, et al., "The Lanthanides as Luminescent Probes in Investigation of Systems", Journal of Photochemistry and Photobiology A: Chemistry, vol. 99, pp. 85-92 (1996).
Gómez-Hens, A., et al., "Terbium-Sensitized Luminescence: A Selective and Versatile Analytical Approach," *Trends in Analytical Chemistry*, vol. 21, No. 2, pp. 131-141 (2002).
Hindle, A., et al., "Dipicolinic Acid (DPA) Assay Revisited and Appraised for Spore Detection," *Analyst*, vol. 124, pp. 1599-1604 (1999).
Horrocks Jr., W., et al., "Lanthanide Ion Lundnescense Probes of the Structure of Biological Macromolecules", *American Chemical Society*, No. 14, pp. 384-392 (1981).
Lamture, et al., Intensity Luminescent Immunoreactive Conjugates of proteins and Dipicolinate-Based Polumeric Tb (III) Chelates, Biconjugate Chemistry, vol. 6, pp. 88-92 (1995).
Lester, E., et al., "An Anthrax "Smoke" Detector", *IEEE Engineering in Medicine and Biology*, pp. 38-42 (Sep./Oct. 2002).
Lutterbach, M.T.S., et al., "Biofilm Formation on Brass Coupons Exposed to Cooling Water", *Brazilian Journal of Chemical Engineering*, vol. 14, No. 1 (Mar. 1997).
Lutterbach, M.T.S., et al., "Biofilm Formation Monitoring in an Industrial Open Water Cooling System," *Revista de Microbiologia*, 28, pp. 106-109 (1997).
Mitchell, A.C., et al., "Measurement of nanosecond time-resolved fluorescence with a directly gated interline CCD camera",Journal of Microscopy, vol. 206, Pt. 3, pp. 233-238 (Jun. 2002).
Nicholson, W.L., et al., "Resistance of *Bacillus endospores* to Extreme Terrestrial and Extraterrestrial Nicholson, Environments", *Microbiology and Molecular Reviews*, vol. 64, No. 3, pp. 548-572 (Sep. 2000).
Partamian, S.A., "Anthrax Detection, The Faster, The Better," *Microbiology 12*, Internet: <http://www.college.ucla.edu/webproject/micro12/honorprojects/Partamianp01/microHonorsWebPage.html pp. 1-8 (Spring 2001).
Pastuszka, J., et al., "Bacterial and fungal aerosol in indoor environment in Upper Silesia, Poland," *Atmospheric Environment*, 34, pp. 3833-3842 (2000).
Pellegrino, P., et al., "Enhanced spore detection using dipicolinate extaction techniques", Analytica Chimicha Acta, vol. 455, No. 2, pp. 1667-177(Jan. 8, 2002).
Pellegrino, P.M., et al., "Bacterial endospore detection using terbium dipicolinate photoluminescence in the presence of chemical and biological materials", Analytical Chemistry 1998 U.S. Army Res. Lab, vol. 70, No. 9, pp. 1755 (1998).
Pierson, D., et al., "Microbial Contamination of Spacecraft", *Gravitational and Space Biology Bulletin* 14 (2) (Jun. 2001).
Rode, L.J., et al., "Induced Release of Dipicolinic Acid From Spores of *Bacillus megaterium*," Department of Bacteriology, The University of Texas, pp. 650-656 (1959).
Rose, L., et al., "Swab Materials and *Bacillus anthracis* Spore Recovery from Nonporous Surfaces", *Emerging Infectious Diseases*, vol. 10, No. 6, www.cdc.gov/eid (Jun. 2004).
Sacks, L.E., "Chemical Germination of Native and Cation-Exchanged Bacterial Spores with Trifluoperazine," *Applied and Environmental Biology*, vol. 56, No. 4, pp. 1185-1187 (1990).
Scholl, P., et al., "Immunoaffinity based phosphorescent sensor platform for the detection of bacterial spores", Proc. Spie Int Soc Opt Eng, Vaol. 3913, pp. 204-214 (2000).
Selvin, P. R., "The renaissance of fluorescence resonance energy transfer," Nature structural Biology, vol. 7, No. 9 (Sep. 2000).
Seveus, et al., "Time-resolved fluorescence imaging of europheu label in immnunohistochemistry and in situ hybridization", Cytometry, 13. pp. 329-338 (1998).
Singh, R., "Microbial Diversity of Biofilms in Dental Unit Water System", *Applied and Environmental Microbiology*, pp. 3412-3420 (Jun. 2003).
Sorasaenee, K., et al., "Cooperative Binding of Tb(III) Supramolecular Complexes with Dipicolinic Acid: Improved Sensitivity of Metal-Contaning Lumophores in Biomedical Applications," *Division of Chemistry and Chemical Engineering, California Institute of Technology*, Pasadena, California, 1 page total (2003).

Uchida, I., et al., "Cloning and Characterization of a Gene Whose Product Is a trans-Activator of Anthrax Toxin Synthesis", *Journal of Bacteriology*, vol. 175, No. 17 (Sep. 1993).

Vaid, A., et al., "The destruction by microwave radiation of bacterial endospores and amplification of the released DNA", *Journal of Applied Microbiology*, vol. 85, pp. 115-122 (1998).

Vereb, G., et al., "Temporarily and Spectrally Resolved Imaging Microscopy of Lanthanide Chelates", Biophysical Journal, vol. 74, pp. 2210-2222 (May 1998).

Warth, A.D., "Liquid Chromatographic Determination of Dipicolinic Acid from Bacterial Spores," *Applied and Environmental Microbiology*, vol. 38, No. 6, pp. 1029-1033 (Dec. 1979).

Xiao, M., et al., "An improved instrument for measuring time-resolved lanthanide emission and resonance energy transfer", *Review of Scientific Instruments*, vol. 70, No. 10 (Oct. 1999).

McBride, et al, Autonomous Detection of Aerosolized *Bacillus anthracis* and *Yersinia pestis, Anal. Chemistry*, (2003) 75, 5293-5299.

Slieman et al, Role of dipocolinic acid in survival of *Bacillus subtilis* spores exposed to artificial and solar UV radiation, *Applied and Environmental Microbiology*, vol. 67, No. 3, 1274-1279, (2001).

Office Communication 96(2) issued by EPO for EP Application No. 02806005.1 dated Jan. 26, 2005.

Office Communication 96(2) issued by EPO for EP Application No. 02806005.1 dated Sep. 15, 2005.

Office Communication 51(4) issued by EPO for EP Application No. 02806005.1 dated Mar. 2, 2007.

Office Communication 96(2) issued by EPO for EP Application No. 03707656.9 dated Jun. 12, 2007.

Notice of Allowance issued by USPTO for U.S. Appl. No. 10/306,331 dated Aug. 15, 2007.

Office Action issued by USPTO for U.S. Appl. No. 10/306,331 dated Jun. 28, 2005.

Office Action issued by USPTO for U.S. Appl. No. 10/306,331 dated Jan. 30, 2006.

Office Action issued by USPTO for U.S. Appl. No. 10/306,331 dated Jul. 13, 2006.

Office Action issued by USPTO for U.S. Appl. No. 10/306,331 dated Apr. 9, 2007.

Office Action issued by USPTO for U.S. Appl. No. 10/355,462 dated Dec. 6, 2004.

Office Action issued by USPTO for U.S. Appl. No. 10/355,462 dated Jun. 2, 2006.

Office Action issued by USPTO for U.S. Appl. No. 10/355,462 dated Feb. 7, 2007.

Restriction Requirement issued by USPTO for U.S. Appl. No. 10/355,462 dated Apr. 21, 2006.

Notice of Allowance issued by USPTO for U.S. Appl. No. 10/987,202 dated Oct. 7, 2008.

Notice of Allowance issued by USPTO for U.S. Appl. No. 10/987,202 dated Jun. 3, 2009.

Office Action issued by USPTO for U.S. Appl. No. 10/987,202 dated Feb. 12, 2007.

Office Action issued by USPTO for U.S. Appl. No. 10/987,202 dated Feb. 25, 2008.

Notice of Allowance issued by USPTO for U.S. Appl. No. 11/332,788 dated Jun. 2, 2009.

Office Action issued by USPTO for U.S. Appl. No. 11/332,788 dated May 30, 2007.

Office Action issued by USPTO for U.S. Appl. No. 11/332,788 dated Nov. 15, 2007.

Office Action issued by USPTO for U.S. Appl. No. 11/332,788 dated Jul. 11, 2008.

Office Communication issued by USPTO for U.S. Appl. No. 11/332,788 dated Jul. 17, 2009.

Restriction Requirement issued by USPTO for U.S. Appl. No. 11/332,788 dated Feb. 7, 2007.

Notice of Allowance issued by USPTO for U.S. Appl. No. 11/404,382 dated Mar. 23, 2009.

Office Action issued by USPTO for U.S. Appl. No. 11/404,382 dated Aug. 16, 2007.

Office Action issued by USPTO for U.S. Appl. No. 11/404,382 dated Jan. 15, 2008.

Office Action issued by USPTO for U.S. Appl. No. 11/404,382 dated Jul. 10, 2008.

Restriction Requirement issued by USPTO for U.S. Appl. No. 11/404,382 dated May 7, 2007.

Office Action issued by USPTO for U.S. Appl. No. 11/453,296 dated Sep. 11, 2009.

Office Action issued by USPTO for U.S. Appl. No. 11/453,296 dated Mar. 6, 2009.

Restriction Requirement issued by USPTO for U.S. Appl. No. 11/453,296 dated Nov. 28, 2008.

International Preliminary Examination Report for PCT/US2002/038005 filed on Nov. 27, 2002 in the name of California Institute of Technology.

International Search Report for PCT/US2002/038005 filed on Nov. 27, 2002 in the name of California Institute of Technology.

International Search Report for PCT/US03/03036 filed on Jan. 31, 2003 in the name of California Institute of Technology.

Byrne, A F., T. H. Burton, et al. (1960). "Relation of dipicolinic acid content of anaerobic bacterial endospores to their heat resistance," Journal of Bacteriology 80(1): 139-140.

Berg, P. E. and N. Grecz (1970). "Relationship of dipicolinic acid content in spores of *Bacillus cereus* to ultraviolet and gamma radiation resistance." Journal of Bacteriology 103(2): 517-519.

Iannasch, H. W., C. O. Wirsen, et al. (1992). "Comparative physiological studies on hyperthermophilic archae a isolated from deep-sea hot vents with emphasis Pyrococcus strain GB-D." Applied and Environmental Microbiology 58: 3472-3481.

Wuytack, E. Y., Boven, S., Michiels, C. W. (1998). "Comparative study of pressure-induced germination of *Bacillus subtilis* spores at low and high pressures." Applied and Environmental Microbiology 64(9): 3220-3224.

Cano, R. J. and M. K. Borucki (1995). "Revival and identification of bacterial spores in 25- to 40-millionyear-old Dominican amber." Science 268(5213): 1060-1064.

Dart, R. (1996). Microbiology for the Analytical Chemist. Cambridge, UK, The Royal Society of Chemistry (Abstract only).

Napier, W. M. (2004). "A mechanism for interstellar panspermia." Monthly Notices of the Royal Astronomical Society 384( 1): 46-51.

Board, S. S. and N. R. Council (2000). Preventing the Forward Contamination of Europa. Washington, D.C., National Academy Press.

Hashimot.T, W. R. Frieben, et al. (1969). "Micro germination of *Bacillus cereus* spores." Journal of Bacteriology 100(3): 1385-1392.

Setlow, P. (2003). "Spore germination." Current Opinion in Microbiology 6(6): 550-556.

Foster, S. J. and K. Johnstone (1989). "Pulling the trigger: the mechanism of bacterial spore germination." Molecular Microbiology 4(1): 137-141.

Moir, A and D. A Smith (1990). "The genetics of bacterial spore germination." Annual Review of Microbiology 44: 531-553.

Jones, G., Vullev, V. I. (2002). "Medium effects on the photophysical properties of terbium(III) complexes with pyridine-2,6-dicarboxylate." Photochemical & Photobiological Sciences 1(12): 925-933.

Fritze, D., Pukall, R. (2001). "Reclassification of bioindicator strains *Bacillus subtilis* DSM 675 and *Bacillus subtilis* DSM 2277 as *Bacillus atrophaeus*." International Journal of Systematic and Evolutionary Microbiology 51: 35-37.

Woese, C. R., H. J. Morowitz, et al. (1958). "Analysis of action of L-alanine analogues in spore germination." Journal of Bacteriology 76(6): 578-588.

Stewart, G. S., K. Johnstone, et al. (1981). "Commitment of bacterial spores to germinate. A measure of the trigger reaction," Biochemical Journal 198(1): 101-106.

Ronner, U., U. Husmark, et al. (1990). "Adhesion of *bacillus* spores in relation to hydrophobicity." Journal of Applied Bacteriology 69(4): 550-556.

Marshall, K. C., R. Stout, et al. (1971). "Mechanism of the initial events in the sorption of marine bacteria to surfaces." Journal of General Microbiology 68: 337-348.
La Due, M. T., Nicholson, W., Kern, R., Venkateswaran, K. (2003). "Microbial characterization of the Mars Odyssey spacecraft and its encapsulation facility." Environmental Microbiology 5(10): 977-985.
Taylor, M. T., P. Belgrader, et al. (2001). "Lysing bacterial spores by sonication through a flexible interface in a micro fluidic system." Analytical Chemistry 73(3): 492-496.
Venkateswaran, K., Chung, S., Allton, J., Kern, R. (2004). "Evaluation of various cleaning methods to remove *bacillus* spores from spacecraft hardware materials." Astrobiology 4(3): 377-90.
C. Edwards, "Environmental Monitoring of Bacteria: Methods in Biotechnology". Totowa, N. J.: Humana Press, 1999 (Abstract Only).
Kempf, M. J. and M. J. McBride. 2000. Transposon insertions in the *Flavobacterium johnsoniae ftsX* gene disrupt gliding motility and cell division. *J. Bacteriol.* 182: 1671-1679.
D. Jan, "AEMC Technology Development Requirements". 1998.
D. L. Pierson, L. Stetzenbach, and C. M. Ott, "Microbial Evaluation of Mir Condensate and Implications for the International Space Station,". Retrieved from http://www.dsls.usra.edu/meetings/bio2001/pdf/abstracts/175p.pdf on Dec. 10, 2009.
P. Barry, "Microscopic Stowaways on the ISS". NASA, Human Spaceflight, 2002. Retrieved from http://spaceflight.nasa.gov/living/factsheets/microstow.html on Dec. 10, 2009,
A. Onion, "Combating Bugs in Space—Tiny Microbes Can Pose Big Problems in Space". ABC News, 2000. Retrieved from http://abcnews.go.com/Technology/story?id=119882&page=1 on Dec. 10, 2009.
A. Ponce, "Live/Dead Spore Assay Using DPA-Triggered Tb Luminescence," *NASA Tech Briefs*, vol. 27, pp. 33-34, 2003.
Archived image of RavenLabs, "http://www.ravenlabs.com", from Apr. 6, 2005.
C.S. Cox and C.M. Wathes, Review of *Bioaerosols Handbook* by John Bartlett. New York: Lewis Publishers, 1995.
Archived image of Universal Detection Technology, "www.udetection.com", from Apr. 14, 2006.
Supplementary European Search Report issued Feb. 15, 2007 for EP 03707656 filed Jan. 31, 2003 in the name of California Institute of Technology.
Supplementary Partial European Search Report issued Nov. 27, 2006 for EP 03707656 filed Jan. 31, 2003 in the name of California Institute of Technology.
Cable, M.L., et al. Bacterial Spore Detection by [Tb 3+ (macrocycle)(dipicolinate)] Luminescence. *J. Am. Chem. Soc.*, 2007, 129 (6), pp. 1474-1475.
P.M. Holland. R.D. Abramson, R. Watson. and D.H. Gelfand, "Detection of specific polymerase chain reaction product by utilizing the 5'-3' exonuclease activity of *thermus-aquaticus* DNA-polymerase," in Proc. Nat. Acad. Sci. USA, vol. 88. 1991. pp. 7276-7280.
Koehler, T.M. *Bacillus anthracis* Genetics and Virulence Gene Regulation. Current Topics in Microbiology and Immunology, 271, pp. 143-164 (2002).
Murrell, W.G. Chemical Composition of Spores and Spore Structures. The Bacterial Spore, ed. Gould, G.W. and Hurst, A., Chapter 7, pp. 213-273. (1969).
Rosen, D.L. Bacterial Endospore Detection Using Photoluminescence from Terbium Dipicolinate. Reviews Analytical Chemistry, vol. 18, No. 1-2, pp. 1-21 (1999).
Notification of Reason for Rejection issued by Japanese Patent Office for JP Application No. 2003-564558 dated Dec. 12, 2008.
Yung, P.T. et al. "Fast Sterility Assessment by Germinable-Endospore Biodosimetry". Applied and Environmental Microbiology, vol. 74, No. 24, pp. 7669-7674, Dec. 2008.
Supplementary European Search Report mailed Nov. 22, 2004 for European Application EP 02 80 6005 filed on Nov. 27, 2002 in the name of California Institute of Technology.
Non-Final Office Action mailed Oct. 5, 2010 for U.S. Appl. No. 12/553,938 filed on Sep. 3, 2009 in the name of Adrian Ponce.
Non-Final Office Action mailed Oct. 7, 2010 for U.S. Appl. No. 12/553,952 filed on Sep. 3, 2009 in the name of Adrian Ponce.
Non-Final Office Action mailed Sep. 27, 2011 for U.S. Appl. No. 11/453,296 filed on Jun. 13, 2006 in the name of Adrian Ponce.
Buttner, Mark P. et al. Monitoring Airborne Fungal Spores in an Experimental Indoor Environment to Evaluate Sampling Methods and the Effects of Human Activity on Air Sampling. Applied and Environmental Microbiology, Jan. 1993, vol. 59, No. 1, pp. 219-226.
Buttner, Mark P. et al. Enhanced Detection of Surface-Associated Bacteria in Indoor Environments by Quantitative PCR. Applied and Environmental Microbiology, Jun. 2001, vol. 67, No. 6, pp. 2564-2570.

* cited by examiner

DPA Tb$^{3+}$

METHODS AND APPARATUS AND ASSAYS OF BACTERIAL SPORES

RELATED APPLICATIONS

The present application is a continuation of U.S. patent application Ser. No. 10/355,462, filed Jan. 31, 2003, now abandoned; which is related to U.S. Provisional Patent Application Ser. No. 60/353,268 filed on Feb. 1, 2002; U.S. Provisional Patent Application Ser. No. 60/395,372 filed on Jul. 12, 2002; and U.S. Provisional Patent Application Ser. No. 60/414,170 filed on Sep. 27, 2002, each of which is incorporated herein by reference and to which priority is claimed pursuant to 35 USC 119.

BACKGROUND OF THE INVENTION

1. Field of the Invention

The invention is directed assays of bacterial endospore levels.

2. Description of the Prior Art

The prior art for species-specific bacterial spore detection, using the lateral flow immunoassay method, is based on observing the red color of gold nanoparticles. It uses two antibodies, in combination, to specifically detect the bacterial spore species of interest in solution. One of the antibodies is attached to a colloidal gold nanoparticle, and the other antibody is immobilized on the nitrocellulose membrane downstream from the point of sample introduction. When about 100 μl of sample is added to the test strip membrane on top of the area 30 that contains the colloidal gold labeled antibodies, specific binding between bacterial spores and gold labeled antibodies occurs. Simultaneously, capillary action moves the gold labeled antibodies (both spore bound and not bound) along the strip membrane 32. In the sample region 34 of the test strip 32 (downstream), specific binding of a second antibody captures bacterial spores with the attached colloidal gold labeled antibody, which gives rise to a red line in the sample region 34 due to the immobilized gold nanoparticles as shown in the bottom left of FIG. 1. In the control region 36 of the test strip 32 (further downstream), as an internal control, a polyclonal antibody binds the gold labeled antibodies that did not bind bacterial spores of interest, which also gives rise to a red line. Thus, observation of two bands, one each in the sample and control regions, indicates a positive test for the bacterial spore of interest. The observation of only one band as shown in the bottom right of FIG. 1 is a negative test result. The fundamental limitation of this method is its sensitivity; a minimum concentration of $10^5$ spores/ml is needed before the red color from the gold nanoparticles becomes detectable; for reference, a 100 μl sample containing 10,000 anthrax spores is lethal.

Therefore what is needed is a method for improving the detection limit of lateral flow immunoassay based detection of bacterial spores, which is reported to be $10^5$ spores/ml. This prior art detection limit prevents detection of trace quantities of bacterial spores. A trace quantity of 8000 anthrax spores, for example, is enough fill a person.

The prior art the method for determining the fraction of viable bacterial spores is based on two measurements. First, the viable bacterial spore count is measured by colony counting, and second, the total bacterial spore count is measured by direct microscopic counting. The ratio of viable to total bacterial spore count yields the fraction of spores that remain viable within a given sample. The procedure for colony counting to determine endospore concentration is comprised of the steps of (1) heat shocking the sample to kill vegetative cells while bacterial spores remain viable, (2) plating a known volume of the sample with a known dilution factor onto a growth medium, and (3) incubating the growth plates for 2 days. Finally, the resulting visible colonies are counted and reported as colony forming units (CFU's). The procedure for direct microscopic counting is comprised of the steps of (1) placing the sample on a slide with an indentation of a known volume. The glass surface of the slide is inscribed with squares of known area. (2) The bacteria in each of the several squares are counted and the average count is multiplied by an appropriate factor to yield the number of total cells per milliliter in the original suspension.

These methods suffer prohibitive difficulties with low concentration samples collected in the field. First, bacterial spores tend to attach themselves onto particulates (dust etc.) and may easily represent the bulk of the biomass in a field sample. Unfortunately, attached bacterial spores cannot be counted with either colony counting or direct microscopic counting. Second, colony-counting methods only work for cultivable bacteria, which are in the minority in field samples (<10% of microbial species form colonies). Finally, the traditional methods are lengthy (>2 days) and labor intensive. These problems have made quantification of low concentration field samples extremely difficult, and have subsequently prevented the application of these methods towards a reliable and/or real-time bacterial spore live/dead assay.

There is a need to develop a live/dead assay for bacterial spores, because there is a need to measure the fraction of bacterial spores that remain viable for samples exposed to harsh environmental conditions such as desert and arctic environments. In terms of planetary protection, which is primarily concerned with spacecraft sterilization, in order to improve sterilization procedures, one must measure the fraction of viable spores after completion of various sterilization protocols. The samples of interest contain low bacterial spore concentration and many particulates, for which the prior art methods useless.

Prior art methods for monitoring aerosolized bacterial spores includes air filtering with subsequent PCR analysis of gene segments from species of interest, and aerosol sampling with subsequent culturing and colony counting. The PCR based method is strongly dependent on impurities in the air, such as city pollution, and requires specially trained technicians to perform sample preparation prior to running the PCR reaction. The procedure for colony counting, which is comprised of (1) heat shocking the sample to kill vegetative cells while bacterial spores remain viable, (2) plating a known volume of the sample with a known dilution factor onto a growth medium, (3) incubating the growth plates for two days, also requires the active participation of a technician. This also assumes that the spore forming microbes are cultivable. It is estimated that only 10% of bacterial species are cultivable. The cost of labor, technical complexity of PCR and slow response time of colony counting have prevented the wide spread application of these methods for monitoring of bacterial spores in the air.

SUMMARY

Synthesis of one form of a lanthanide complex according to the invention is shown in the embodiment diagrammed in FIG. 9 where ethylene diaminetetraaceticacid zwitterion (EZ) molecule is depicted. In refluxing ethanol (2-aminoethyl)trimethylammonium chloride hydrochloride is insoluble, however the free base (2-aminoethyl)trimethylammonium chloride, is soluble, and is generated in solution with sodium hydroxide. A metathesis reaction occurs, and fine microcrystals of sodium chloride precipitate from the hot ethanol mixture, leaving an ethanol solution of the freebase (2-aminoethyl)trimethylammonium chloride. To this solution is added ethylene diamine tetra-acetic acid (EDTA) dianhydride, which reacts with the primary amine group of the two equivalents of (2-aminoethyl)trimethylammonium chloride. This reaction yields EZ in its carboxylic acid form. To produce the zwitterionic form of EZ, two extra equivalents of the free base amine are added to deprotonate this intermediate carboxylic acid yielding EZ and (2-aminoethyl)trimethylammonium chloride hydrochloride which is insoluble in ethanol and easily filtered away form the solution. It must be understood that many other forms and syntheses of lanthanide ions in the form of lanthanide complex are possible and expressly contemplated as being within the scope of the invention. Each of the alternative forms will combine with the medium as an analysis reagent which is capable of cooperative binding with dipicolinic acid from endospores to increase both the lanthanide-dipicolinic acid binding constant and the luminescence quantum yield.

The enhancement in the binding of a DPA molecule to the Tb3+ is the result of several factors at play in the ternary complex of a DPA molecule, a Tb3+ ion and EZ molecule. First the EZ molecule acts as a template or foundation capturing a Tb3+ with the amine and carboxylate groups at the core of the molecule to yield a complex (EZ-Tb)3+. Notice that the overall charge of this complex is 3+, but that two units of charge have effectively migrated out to the trimethylammonium groups at the ends of the molecule, which are not involved in the coordination the EZ molecule to the Tb3+ ion. FIG. 10 is a graph of the experimental data showing the enhanced intensity in detection of DPA (M) using the EZ molecule to complex with Tb.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

Lateral Flow Immunoassay

One embodiment of the invention is defined as a method for lateral flow immunoassay for bacterial spore detection and quantification comprising the steps of providing a matrix including terbium ions, releasing DPA from the bacterial spores, combining the terbium ions with the DPA in solution, and exciting the combined terbium ions and DPA to generate a luminescence characteristic of the combined terbium ions and DPA to detect the bacterial spores. The matrix The detection of the spores or their concentration above a predetermined threshold generates an alarm signal.

The DPA is released from the bacterial spores by microwaving the spores, germinating the spores with L-alanine, sonicating the spores with microspheres or autoclaving the spores. These methods by no means necessarily exhaust the ways in which the DPA can be released from the spores and all other methods of lysing the spores are deemed equivalent.

Exciting the combined terbium ions and DPA generates a luminescence characteristic of the combined terbium ions and DPA. This is achieved by radiating the combined terbium ions and DPA with ultraviolet light. Again, any method by which luminescence can be induced is included within the scope of the invention and is deemed to be equivalent.

The invention can also be characterized as a method for lateral flow immunoassay for bacterial spore detection and quantification. The method starts with the step of adding a sample of unknown bacterial spores to a test strip. The sample of unknown bacterial spores is drawn to a first sample region on the test strip by capillary action. Species-specific antibodies are bound to the sample when the unknown bacterial spores match the species-specific antibodies, otherwise the sample is left unbound. DPA is released from the bacterial spores in the bound sample. The terbium ions are combined with the DPA to form a Tb-DPA complex. The combined terbium ions and DPA are excited to generate a luminescence characteristic of the combined terbium ions and DPA to detect the bacterial spores.

The method further comprises the steps of performing the same steps with a standard of known bacterial spores with known concentration. The sample is added to the test strip and drawn to a second sample region on the test strip. Species-specific antibodies are selectively bound to the standard when the known bacterial spores match the species-specific antibodies, otherwise the standard unbound is left unbound. DPA is released from the bacterial spores in the bound standard and combined with the terbium ions. The combined terbium ions and DPA are excited to generate a luminescence characteristic of the combined terbium ions and DPA to detect the bacterial spores of the standard. The intensity of the excited luminescence from the sample is compared with the excited luminescence from the standard to derive a quantification of the spore concentration in the sample. The method may further comprise the step of confirming arrival of the sample and standard in the first and second sample regions respectively by means of a visual indicator.

Live/Dead Assay for Bacterial Spores

The invention is defined in another embodiment as a method for live/dead assay for bacterial spores comprising the steps of: providing a solution including terbium ions in a sample of live and dead bacterial spores; releasing DPA from viable bacterial spores by germination from a first unit of the sample; combining the terbium ions with the DPA in solution released from viable bacterial spores; exciting the combined terbium ions and DPA released from viable bacterial spores to generate a first luminescence characteristic of the combined terbium ions and DPA to detect the viable bacterial spores; releasing DPA from dead bacterial spores in a second unit of the sample by autoclaving, sonication or microwaving; combining the terbium ions with the DPA in solution released from dead bacterial spores; exciting the combined terbium ions and DPA released from dead bacterial spores to generate a second luminescence characteristic of the combined terbium ions and DPA to detect the dead bacterial spores; generating a ratio of the first to second luminescence to yield a fraction of bacterial spores which are alive.

Lifetime-Gated Measurements of Bacterial Spores and Imaging Bacterial Spores Using an Active Pixel Sensor In yet another embodiment the invention is a method for lifetime-gated measurements of bacterial spores to eliminate any fluorescence background from organic chromophores comprising the steps of providing a solution including terbium ions with a sample of bacterial spores; labeling the bacterial spore contents with a long-lifetime lumophore; releasing DPA from the bacterial spores; combining the terbium ions with the DPA in solution; exciting the combined terbium ions and DPA for a first time period; waiting a second time period before detecting luminescence; and detecting a luminescence characteristic of the combined terbium ions and DPA after the second time period during a defined temporal window synchronized with luminescence timed from the long lifetime lumophore to detect the bacterial spores.

In one embodiment the first time period of excitation is of the order of nanoseconds, the second time period is of the order of microseconds and the defined temporal window is of the order of milliseconds.

In another embodiment the first time period of excitation is of the order of 1-10 nanoseconds, where the second time period is of the order of tens of microseconds and where the defined temporal window is of the order of 1-10 milliseconds.

In still another embodiment the first time period of excitation is of the order of nanoseconds, the second time period is of the order of tenths to tens of milliseconds and where the defined temporal window is of the order of hundreds of microseconds.

Unattended Monitoring of Bacterial Spores in the Air

In yet another embodiment the invention is a method for unattended monitoring of bacterial spores in the air comprising the steps of collecting bacterial spores carried in the air; suspending the collected bacterial spores in a solution including terbium ions; releasing DPA from the bacterial spores; combining the terbium ions with the DPA in solution; exciting the combined terbium ions and DPA to generate a luminescence characteristic of the combined terbium ions and DPA; detecting the luminescence to determine the presence of the bacterial spores; and generating an alarm signal when the presence of bacterial spores is detected or the concentration thereof reaches a predetermined magnitude.

The step of collecting bacterial spores carried in the air comprises capturing the bacterial spores with an aerosol sampler or impactor. The step of detecting the luminescence to determine the presence of the bacterial spores comprises monitoring the luminescence with a spectrometer or fluorimeter.

Preferably, the step of collecting bacterial spores carried in the air comprises continuously sampling the air and the step of detecting the luminescence to determine the presence of the bacterial spores comprises continuously monitoring the luminescence.

When the step of releasing DPA from the bacterial spores comprises microwaving the bacterial spores to heat the solution, the step of combining the terbium ions with the DPA in solution comprises cooling the heated solution to increase the fraction of bound Tb-DPA complex.

The invention is also apparatus for performing the various methods disclosed above. For example, the invention includes an apparatus for unattended monitoring of bacterial spores in the air comprising: a biosampler for capturing the bacterial spores in the air and having a collection vessel containing a solution including terbium ions into which the captured bacterial spores are suspended; means for releasing DPA from the bacterial spores in the solution to allow the DPA to combine with the terbium ions to form a Tb-DPA complex; an energy source for exciting the Tb-DPA complex to generate luminescence; an electro-optical circuit to measure the luminescence; and an alarm circuit coupled to the electro-optical circuit to detect a bacterial spore concentration above a predetermined threshold.

The invention is also an apparatus for lateral flow immunoassay for bacterial spore detection and quantification comprising: a strip of material for providing lateral capillary flow of a solution including terbium ions across the strip; an input region on the strip for receiving a liquid sample containing terbium ions, the first zone being provided with a first antibody for specific binding to a specific specie of bacterial spores; a sample region of the strip laterally displaced from the input region and communicated thereto by means of capillary flow therebetween, the sample region being provided with a second antibody to capture bacterial spores with the attached first antibody and to immobilize them; means for releasing DPA from the bacterial spores in the sample region of the strip to then allow the terbium ions to combine with the DPA in solution; an energy source to excite the combined terbium ions and DPA in the sample region of the strip to generate a luminescence characteristic of the combined terbium ions and DPA; and a luminescence detector to identify the presence or measure the concentration of the bacterial spores in the sample region of the strip.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 4*a* shows the intensity during germination starting with t=0 when L-alanine was added. FIG. 4*b* shows the Tb luminescence after completion of germination corresponding to Tb-DPA complex. FIG. 4*c* shows Tb luminescence induced by autoclaving.

FIG. 8*a* illustrates the time course of spore monitoring and FIG. 8*b* shows the spectrum just before spore release, less than 15 minutes after spore release and 60 minutes after spore release.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Lateral Flow Immunoassay

The invention is directed to lateral flow immunoassay for bacterial spore detection and quantification using lanthanide luminescence with both high sensitivity and selectivity in less than five minutes. The method combines lateral flow immunoassay and dipicolinic acid (DPA) triggered terbium (Tb) luminescence technologies. The lateral flow immunoassay provides high selectivity for specific bacterial spore species, and the DPA triggered Tb luminescence method for bacterial spore detection enables greatly improved detection limits over the prior art detection schemes.

The new technology has significantly improved detection limits, because it is based on Luminescence turn-on against a dark background, which is much more sensitive than measuring the scattered light, from gold nanoparticles against a bright background. Based on DPA-triggered Tb luminescence experiments, we anticipate single spore detection limits for 100 μl samples (i.e. 10 spores/ml).

The solution for developing a lateral flow immunoassay based detection of bacterial spores with single spore detection limits is to use DPA triggered Tb luminescence as the detection scheme. The methodology for achieving single spore detection is more expressly disclosed in copending U.S. patent application entitled "An Improvement In A Method For Bacterial Endospore Quantification Using Lanthanide Dipicolinate Luminescence," Ser. No. 10/306,331 filed on Nov. 27, 2002 and assigned to the same assignee as the present invention, which application is incorporated herein by reference.

Figure 1:
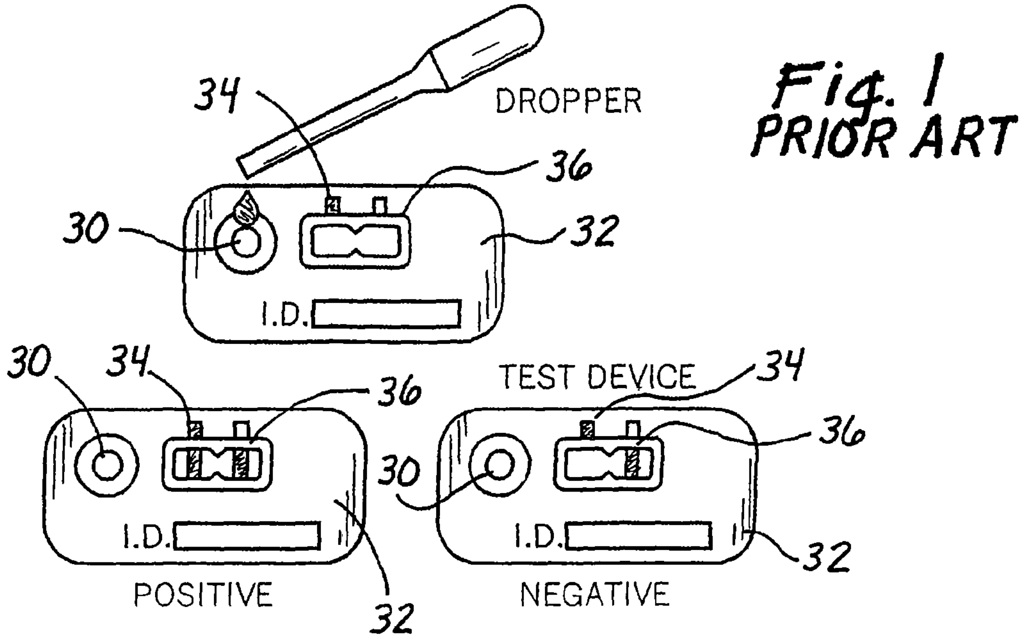
FIG. 1 is a diagram of a prior art lateral flow immunoassay for bacterial spores.
Figure 2A:
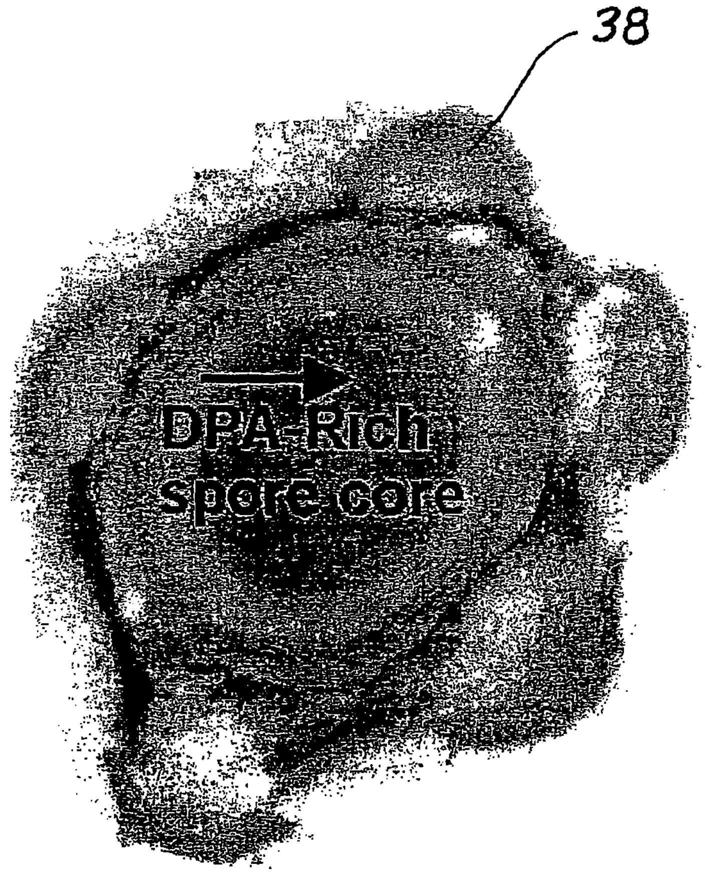
FIG. 2*a* is a microscopic image of a spore (about 1 μm in diameter) highlighting a DPA rich spore core.
Figure 2B:
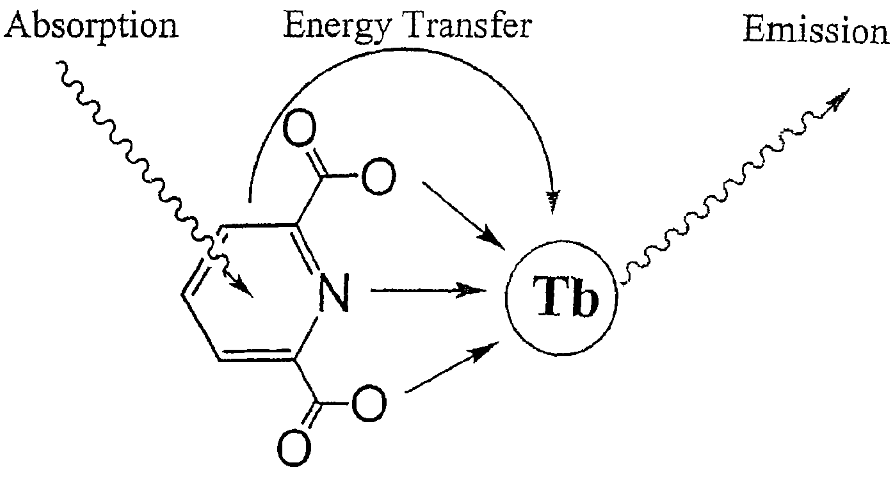
FIG. 2*b* is a diagram of a $Tb^{3+}$ ion (shaded ball) by itself has a low absorption cross section (<10 $M^{-1}$ $cm^{-1}$) and consequently has low luminescence intensity. The $Tb^{3+}$ ion can bind the light harvesting DPA (absorption cross section >$10^4$ $M^{-1}$) originating from the spore; DPA binding gives rise to bright Tb luminescence.
Figure 2C:
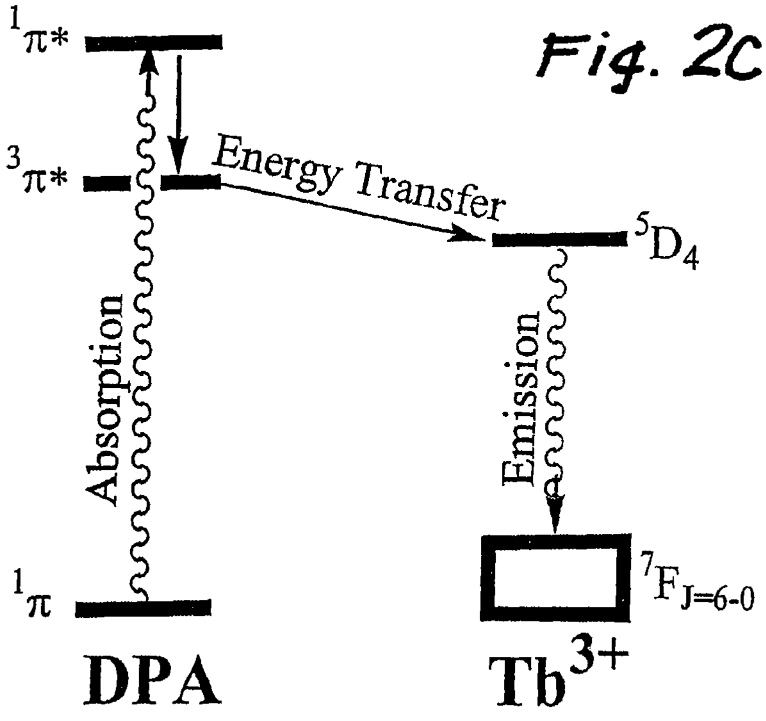
FIG. 2*c* is a diagram of a photophysical scheme for DPA sensitized luminescence of the Tb complex (absorption-energy transfer-emission, AETE).

Consider now the DPA-triggered Tb luminescence detection of bacterial spores. Dipicolinic acid DPA, 2,6 pyridinedicarboxylic acid) is present in high concentrations (about 1 molar or about 15% of by weight) in the core of bacterial spores 38 as a 1:1 complex with $Ca^{2+}$ as shown in FIG. 2*a*. For all known lifeforms, DPA is unique to bacterial spores and is released into bulk solution upon germination, which is the process of spore-to-vegetative cell transformation. Thus, DPA is an indicator molecule for the presence of bacterial spores. Fortuitously, DPA is also a classic inorganic chemistry ligand that binds metal ions with high affinity. DPA binding to terbium ions triggers intense green luminescence under UV excitation as shown in FIGS. 2*b* and 2*c*. Thus, the green luminescence turn-on signals the presence of bacterial spores, and the intensity of the luminescence can be correlated to the number of bacterial spores per milliliter. Potential interferents such as sugars, nucleic and amino acids are present in much lower concentrations in endospores and vegetative cells and have binding constants for Tb that are approximately six orders of magnitude less than that of DPA ($K_A=10^{8.7}$ $M^{-1}$). This method is relatively immune to these interferents.

The core of bacterial spores contains 1 molar dipicolinic acid (DPA) (~15% of the spore dry weight). It has been shown that the DPA can be released into bulk solution by microwaving the sample (germination with Lalanine, sonication with microspheres, and autoclaving have also been used to release DPA from the spore). When the released DPA binds terbium ions in bulk solution, bright green luminescence is triggered under UV excitation.

The mechanism of DPA-triggered Tb luminescence is based on the unique photophysical properties of lanthanide ions. The luminescence of lanthanide ions is characterized by long lifetimes (0.1 to 1 ms), small extinction coefficients (a.k.a. absorbtivity, about 1 $M^{-1}$ $cm^{-1}$) and narrow emission bands. These characteristics arise because the valence f orbitals are shielded from the environment by the outer 5s and 5p electrons, and because the transition between the emitting excited stare and ground state is highly forbidden. Thus, direct excitation of terbium ions leads to weak luminescence due to the small absorption cross section. However, coordination of aromatic chromophores, like DPA, triggers intense terbium luminescence. The juxtaposition of DPA, which has an absorbtivity of 5000 $M^{-1}$ $cm^{-1}$ serves as a light-harvesting center (e.g. antenna effect). Strong electronic coupling and downhill energies allow the DPA centered excitation energy to be efficiently transferred to the lanthanide ion, which subsequently luminesces bright green.

Figure 3:
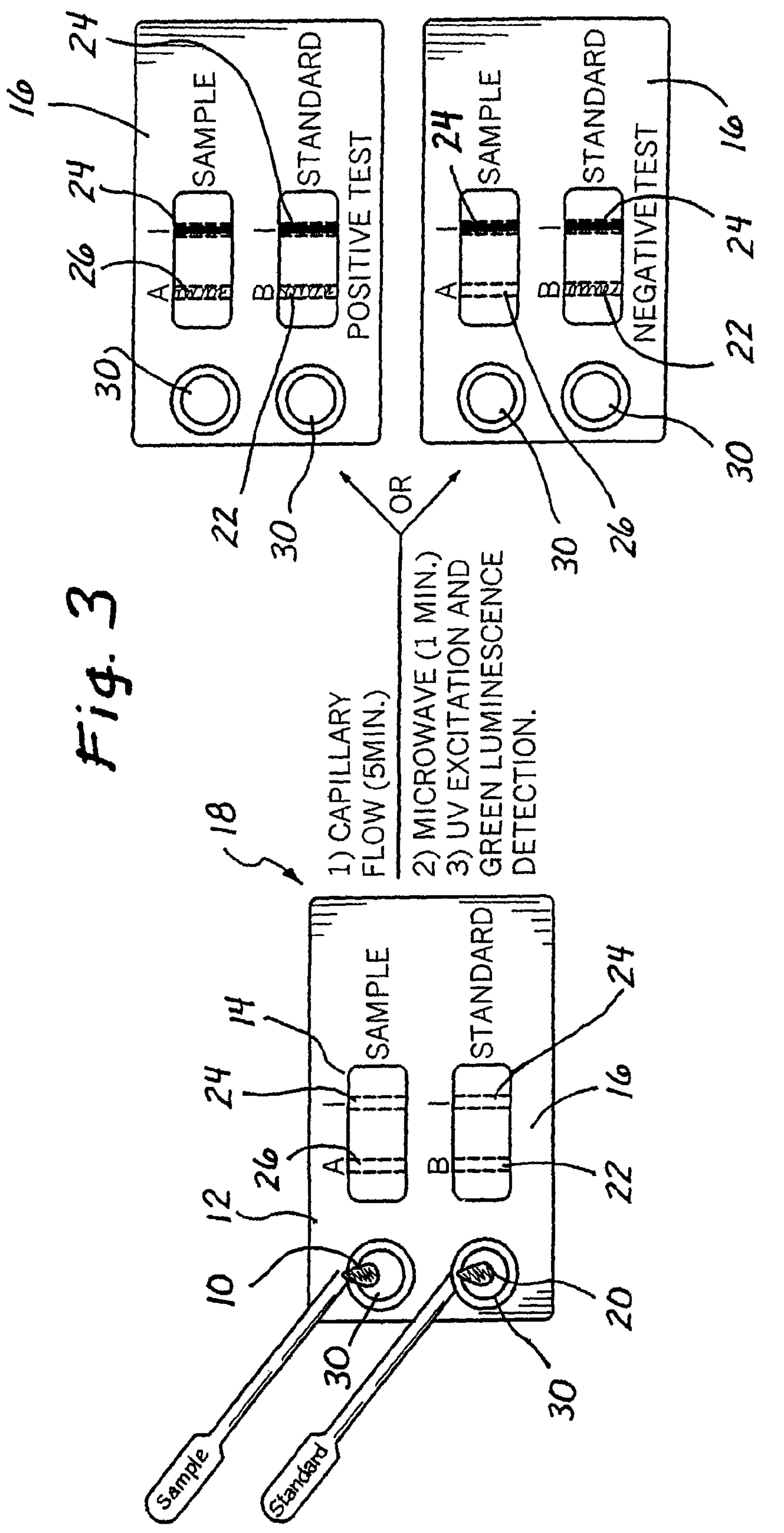
FIG. 3 is a diagrammatic illustration showing a few drops of bacterial spore containing sample are added to the test strip membrane.

Consider now the details of lateral flow immunoassay with DPA-triggered Tb luminescence detection of bacterial spores 10. The test strip 18 is comprised of a nitrocellulose membrane 12 that has species-specific antibodies bound in the sample regions, which are regions 26 and 22 of the strip as shown in FIG. 3. Region 26 contains antibodies for the bacterial spore species 10 of interest (e.g. *B. anthracis* antibody), and region 22 contains antibodies for *B. subtilis* (standard 20). First, about 100 μl of sample 10 in a liquid, such as water, and standard 20 in a solution of the same or a different liquid are added to their respective test strip membranes 12 and 16 in the sample port region 30. Capillary action moves the spores 10 along the strip membrane 12 and 16. In the sample region 14 of the test strip 12 (downstream), specific binding of membrane-bound antibodies captures and immobilizes the bacterial spores 10, while components of the sample 10 that do not bind the antibody continue to flow out of the sample region 14. Regions 24 contain an indicator, such as cobalt chloride, that changes visible color when the liquid or solvent front arrives, after about five minutes, which should suffice to provide adequate separation of the specific binding components to the nonspecific components of the sample 10. For example, where the indicator is cobalt chloride, the color changes to blue to pink on arrival of the liquid, which is in this embodiment is water. The choice of liquid and indicator is a matter of design choice and many other selections can be equivalently substituted.

In the next step, DPA is released from the core of the spores 10 by microwaving the test strip 12. The released DPA binds Tb dissolved in the solution and triggers green luminescence, which signals the presence of bacterial spores. The green luminescence can be read or measured by a conventional spectrometer or fluorometer (not shown).

The control is performed on a parallel test strip to which about 100 μl containing a known concentration of *Bacillus subtilis* is added. The standard 20 undergoes the identical procedure as the unknown sample 10. Green luminescence in region 22 and a change in color in regions 24 indicates that the assay has worked properly and the ratio of luminescence intensity from the sample 10 in region 26 and standard 20 in region 22 is proportional to the concentration of the bacterial spore of interest. The microwaving step can be completed in less than 2 minutes. Thus the complete assay can be performed within 7 to 10 minutes. The sample 10 and standard 20 may be processed simultaneously or sequentially as may be desired.

Live/Dead Assay for Bacterial Spores

The invention also includes a method and apparatus to measure the fraction of bacterial spores that remain viable or alive, hence a live/dead assay for bacterial spores. The method combines dipicolinic acid triggered terbium luminescence and dipicolinic acid release from (1) viable bacterial spore through germination, and (2) all viable and nonviable bacterial spores by autoclaving, sonication, or microwaving. The ratio of the results from steps (1) and (2) yield the fraction of bacterial spores that are alive.

The invention does not suffer from the aforementioned prior art problems of colony or microscopic counting, because it is based on a molecular approach that (1) works whether or not a bacterial spore is attached on a particulate, (2) does not require bacteria to be cultivable, and (3) can be performed on the timescale of 20 minutes.

The solution for developing a live/dead assay for bacterial spores requires a molecular approach. DPA can be released into bulk solution by inducing germination with L-alanine or by autoclaving the sample. In germination, only viable spores release DPA, while autoclaving forces all spores, viable and nonviable, to release DPA. Microwaving and sonication also releases DPA from all spores, whether dead or alive. Again, when the released DPA binds terbium ions in bulk solution, bright green luminescence is triggered under UV excitation.

The luminescence intensity can be correlated to the concentration of viable bacterial spores when germination is used to release the DPA, and to the total bacterial spore concentration when either autoclaving, sonication, or microwaving is used to release DPA. Thus, these methods of DPA release allow us to quantify both the viable and total bacterial spore count, and subsequently the fraction of spores that are viable for a given sample.

Figure 4A:
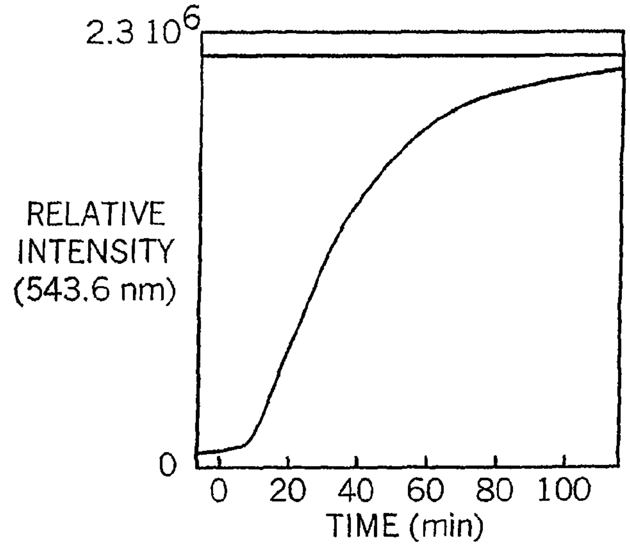
FIGS. 4*a*-4*c* are graphs of the intensity of Tb luminescence verses time.
Figure 4B:
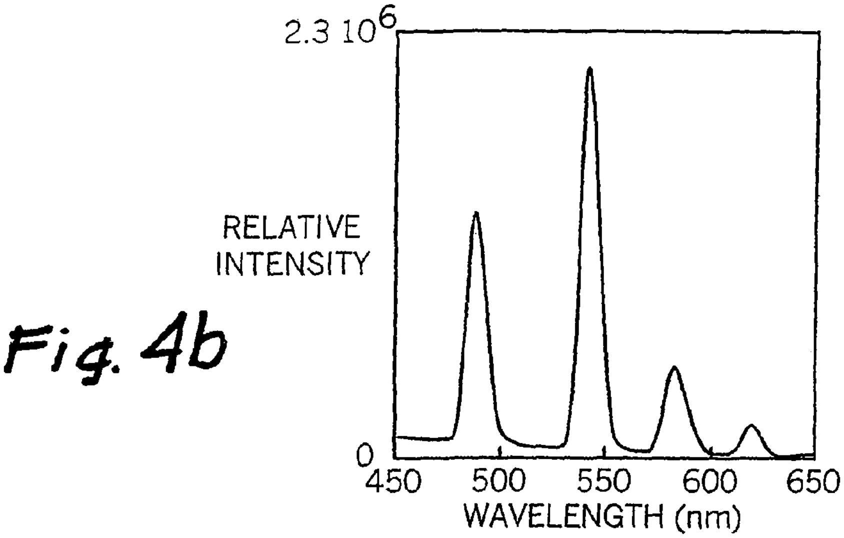
Figure 4C:
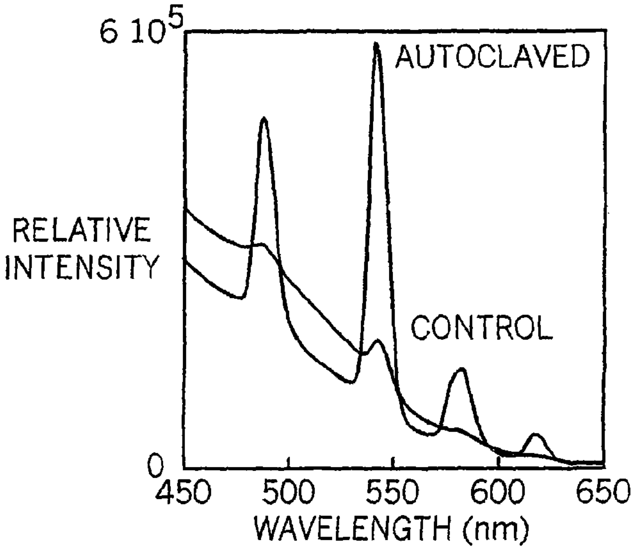

Since germination releases the DPA content of viable bacterial spores, while autoclaving, sonication, and microwaving releases the DPA content of all bacterial spores, including non-viable bacterial spores, using the DPA triggered Tb luminescence method in conjunction with the DPA release, induced by (1) germination and (2) either autoclaving, sonication, and microwaving, allows us to determine the viable and total spore count, respectively, and subsequently the fraction of viable bacterial spores as illustrated in FIGS. 4*a*, 4*b* and 4*c*. FIG. 4*a* shows the time course data of endospore germination monitored by DPA triggered Tb luminescence at 543 nm. Time zero corresponds to L-alanine induced germination. FIG. 4*b* shows the spectrum of the luminescence corresponding to Tb-DPA complex, which is induced after completion of germination. FIG. 4*c* compares the spectrum for an autoclaved sample verses a control sample which is not autoclaved.

Lifetime-Gated Measurements of Bacterial Spores and Imaging Bacterial Spores Using an Active Pixel Sensor Finally, the method of the invention is amenable to lifetime-gated measurements to eliminate any fluorescence background from organic chromophores. It is also possible to quantify the fraction of bacterial spores that remain viable by inducing DPA release by germination and microwaving as described below, and to obtain further increased sensitivity by preparing special Tb complexes that enhance the luminescence turn-on, and DPA binding affinity.

Consider now the problem of imaging bacterial spores. The imaging methodology is again based on a combination of dipicolinic acid triggered terbium luminescence (Tb luminescence assay) and imaging using an active pixel sensor (APS), which is well known to the art. The Tb luminescence assay enables specific detection of bacterial spores with a current detection limit of 5,000 spores/ml when $TbCl_3$ is used as the analysis reagent. This assay can be performed in 30 minutes or less depending on the DPA release mechanism that is employed. APS is ideally suited to image the resultant Tb luminescence when spores are present because of its inherent ability to perform lifetime gated imaging.

In this embodiment the spores or their contents have been labeled with a long-lifetime lumophore which fact is used to advantage during detection. Since almost every natural fluorescent material decays in a few nanoseconds, delayed luminescence is a powerful discriminator against background biological or mineralogical signals. For example, flavinoids, NADH, collagen and many other biological and cellular components fluoresce in the wavelength region of 300-500 nm, but all have lifetimes less than a few tens of nanoseconds.

Jet Propulsion Laboratory has developed a true snapshot imager, using CMOS technology in an APS that is ideally suited for imaging and measurement of delayed luminescence probes. In this implementation, the entire imager can be cycled off and on in a clock cycle, typically less than a microsecond. The basic measurement cycle is to pulse an excitation source for the luminescence with an on time of a few nanoseconds, wait 30 μs and than turn on the imager for 2 ms, turn it off and read out the image and the photon counts for each pixel. A unique feature of the CMOS or Active Pixel Sensor (APS) technology is that each pixel can contain active circuit elements and can perform signal averaging to improve the signal to noise as well as other processing. By imaging the collection tape, we can count the pixels that contain luminescence signal and get a spore count.

Figure 5A:
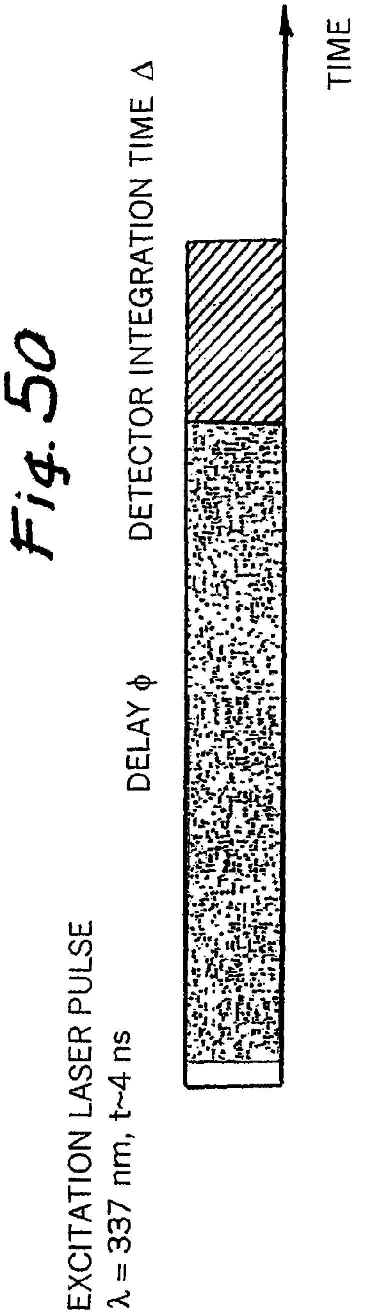
FIGS. 5*a*-5*b* show a diagram and related images illustrating the active pixel sensor imaging method as applied to Tb luminescence in bacterial spores
Figure 5B:
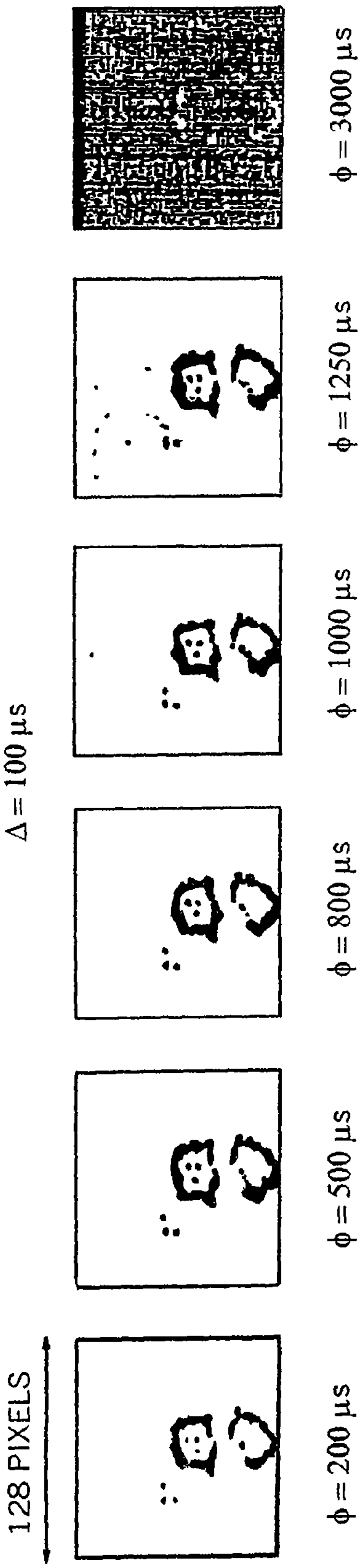
Figure 6:
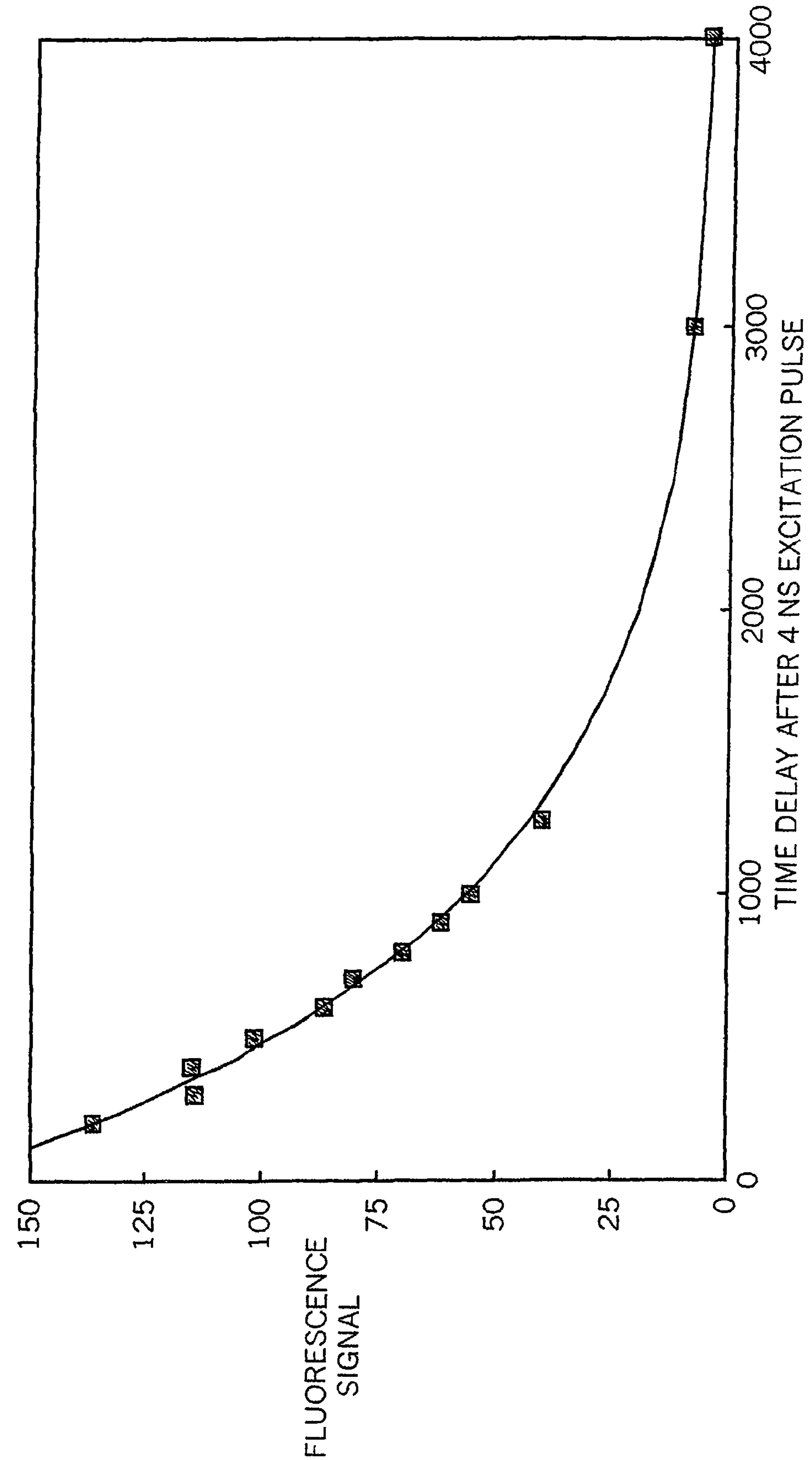
FIG. 6 is the lifetime series decay of the bacterial spores illuminated in FIG. 5.

FIG. 5*a* shows a diagrammatic timing sequence for excitation, a delay $\phi$, and detector integration time $\Delta$. Image data taken with the APS for an Europium probe with a lifetime of ~800 μs is shown in FIG. 5*b* in which we applied a few spots of the Europium probe to an APS 256×256 imager and excited the fluorescence with a pulsed $N_2$ laser at 337 nm and a pulse width of ~4 ns. Excitation can be performed with a compact laser, laser diode or LED. By adjusting the timing of the detection window, delay $\phi$, the decay curve of the fluorophore can be mapped out as shown in FIG. 6, which is a graph of the lifetime data obtained from the images of FIG. 5*b*. The fluorescence signal in FIG. 6 is summed up from all the pixels on the upper spot of the APS sensor as shown in FIG. 5*b*.

Unattended Monitoring of Bacterial Spores in the Air

Consider now the technology that is required to enable one to achieve unattended monitoring of bacterial spores in the air. The novelty of the method lies again in the combination of (1) aerosol capture methods and (2) lanthanide luminescence detection of bacterial spores This combination will enable an alarm for airborne bacterial spores similar in concept to a smoke detector, which works continuously and unattended.

The invention as described below does not suffer from the above mentioned problems of the prior art, because it (1) does not require cultivable bacteria, and (2) can be performed continuously with a sampling rate of at least four readings per hour using current instrumentation, and (3) does not require active sampling by a trained technician.

Online monitoring of aerosolized bacterial spores, such as *Bacillus anthracis* and *Clostridium botulism* spores, is essential in locations such as public transportation, mail sorting, food preparation, health care facilities and even military environments. We have become especially motivated to develop a method of unattended monitoring of bacterial spores in the air after the anthrax attacks following the Sep. 11, 2002 terrorist attacks. Another motivation was the application of the method towards planetary protection, which is primarily concerned with spacecraft sterilization.

A solution for unattended monitoring of airborne bacterial spores is achieved by the combination of (1) aerosol capture methods and (2) lanthanide luminescence detection of the bacterial spores as described above. The luminescence intensity arising from DPA detection can be correlated to the concentration of bacterial spores. When this detection method is coupled to an aerosol capture device that suspends aerosolized spores into a terbium containing solution, unattended monitoring of bacterial spores in the air is enabled.

In general, the method comprises the steps of capturing aerosolized bacterial spores with an aerosol sampler or impactor of which there are many commercial models are available. The captured spores are then lysed using microwave radiation, autoclaving, or other methods that release DPA from the core of the spores. The released DPA then binds terbium ions or other chromophores that give rise to luminescence turn-on upon DPA binding. The luminescence turn-on is monitored by a luminescence spectrometer or fluorimeter. Continuous sampling of the air while monitoring for luminescence turn-on gives rise to an alarm capability for aerosolized bacterial spores, which does not require human participation over extended periods, such as time periods of the order of 8 hours.

Figure 7:
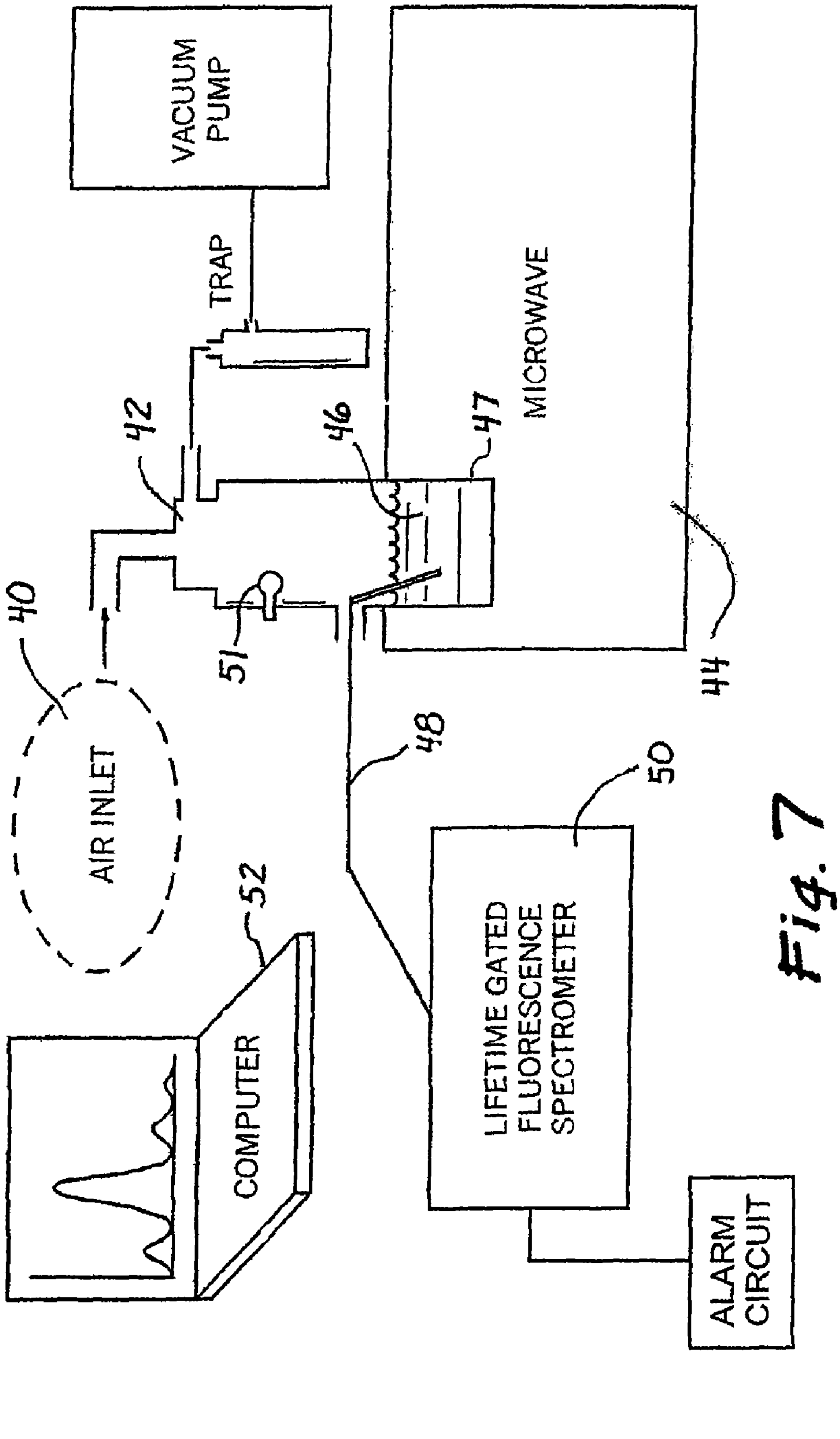
FIG. 7 is a simplified diagram of an unattended air monitor for bacillus using Tb-DPA detection.

In the illustrated embodiment stock solutions of purified *Bacillis subtilis* spores were purchased from Raven Biological. A Lovelace nebulizer was used to generate an aerosol 40 of the bacterial spore air suspensions. The spore "smoke" detector instrument as shown in the diagram of FIG. 7, is comprised of three components: (1) a biosampler 42 for aerosol capture, (2) a microwave with temperature and pressure control 44 for releasing the DPA from the spores, and (3) a lifetime-gated luminescence spectrometer 50 for luminescence detection. The lifetime gating works by exciting the sample with a short Xe-lamp flash 51 and waiting several microseconds before detecting light from the sample 46, thus eliminating the background fluorescence from impurities with 10-ns fluorescent lifetimes.

The biosampler 42, filled with 20 ml of 10 μM $TbCl_3$ glycerol solution, has a 95% transfer efficiency for microbe-containing aerosols. Once bacterial spores are suspended in the biosampler collection vessel 47, microwaving completely or sufficiently releases DPA into bulk solution 46 within 8 minutes or less. The resulting free DPA then binds Tb in bulk solution, giving rise to luminescence turn-on under UV excitation. A fiber optic probe 48 immersed in the sample solution transmits the Luminescence to the spectrometer 50. Spectrometer 50 is coupled to alarm circuit 52 which then generates an appropriate alarm signal when a predetermined detection occurs, namely a wireless or wired signal with identification information is generated and transmitted to a remote monitoring station. The monitoring station may monitor a plurality of remote biosensors such as shown in FIG. 7 and providing a continuous time, date, place and biomeasurement report from them.

Figure 8A:
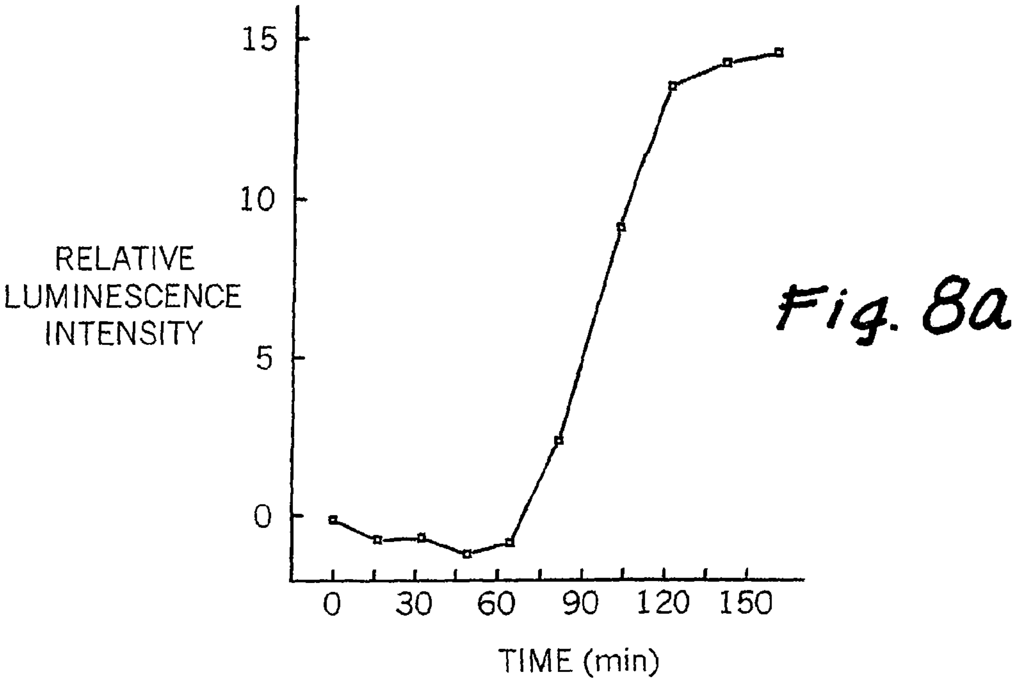
FIGS. 8*a* and 8*b* are graphs of the relative luminescence intensity as a function of time and wavelength respectively.

While the biosampler 42 is continually sampling the air, a cycle comprising an 8-minute microwaving step at 140.degree. C. at 1 atmosphere, a 7 minute cooling period, and a 30 second luminescence measurement is performed repeatedly. Cooling down to room temperature is required because the binding constant for the Tb-DPA complex at 140.degree. C. is much lower than at room temperature, thus leading to near zero fraction bound at 140.degree. C. FIG. 8*a* shows the time course of the luminescence intensity at 543.5 nm versus time for the online monitoring for aerosolized bacterial spores in the device of FIG. 7. After five data points are collected in the time interval between t=0 and 63 minutes, we initiated the nebulizer for 5 minutes to generate aerosolized bacterial spores, which were directed to the inlet of the biosampler 42. The sixth data point at t=81 min. clearly shows the presence of Tb-DPA luminescence, thus signaling the presence of bacterial spores. The luminescence intensity in the plateau region after 130 minutes corresponds to a spore concentration of 10.sup.5 spores/ml. The luminescence increases for two more heating and cooling cycles and then plateaus 60 minutes after the initiation of the spore event.

Figure 8B:
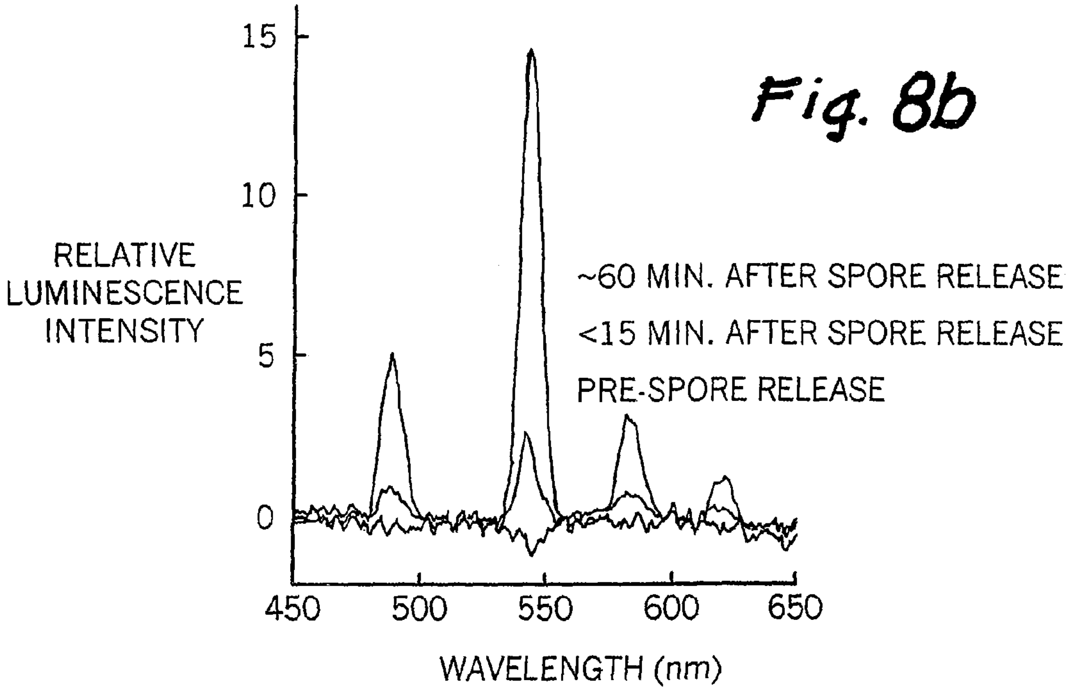
Figure 9:
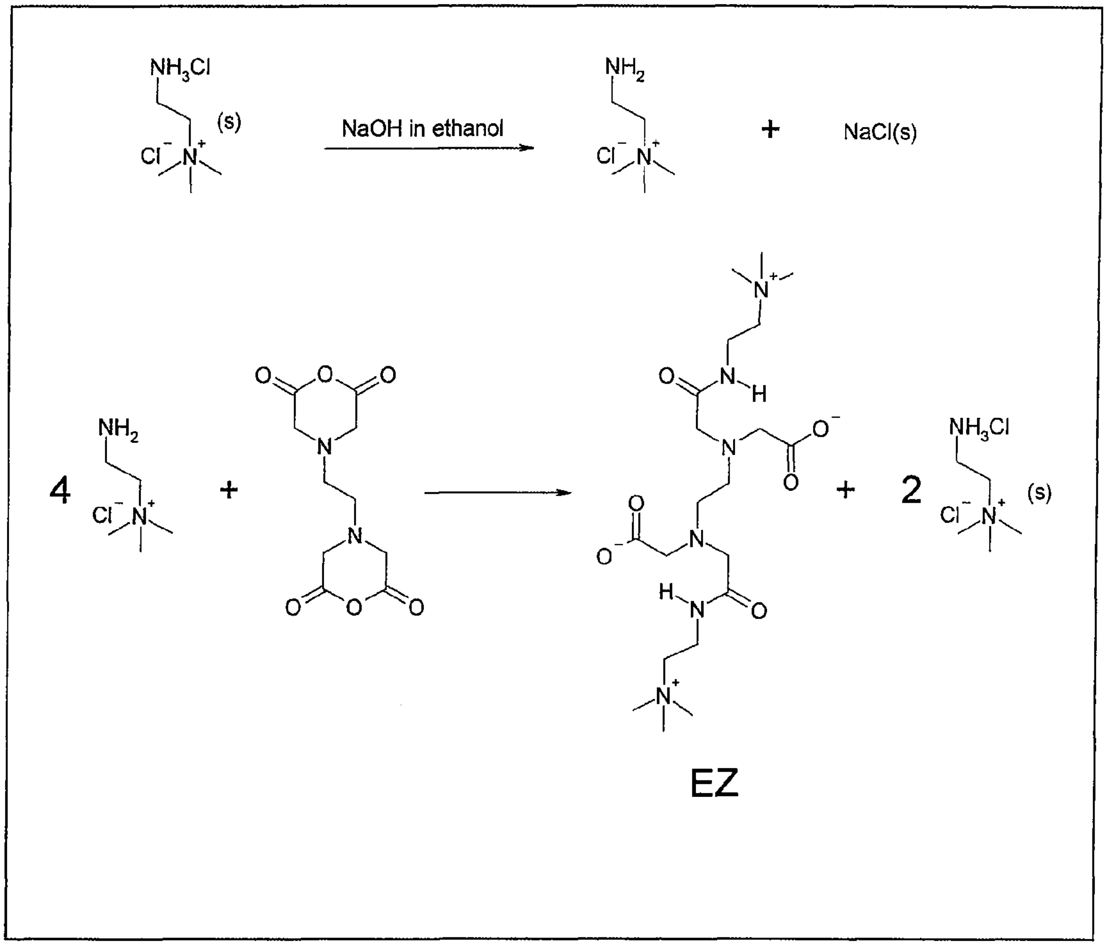
FIG. 9 is a diagram of the ethylene diaminetetraaceticacid zwitterion (EZ) molecule.
Figure 10:
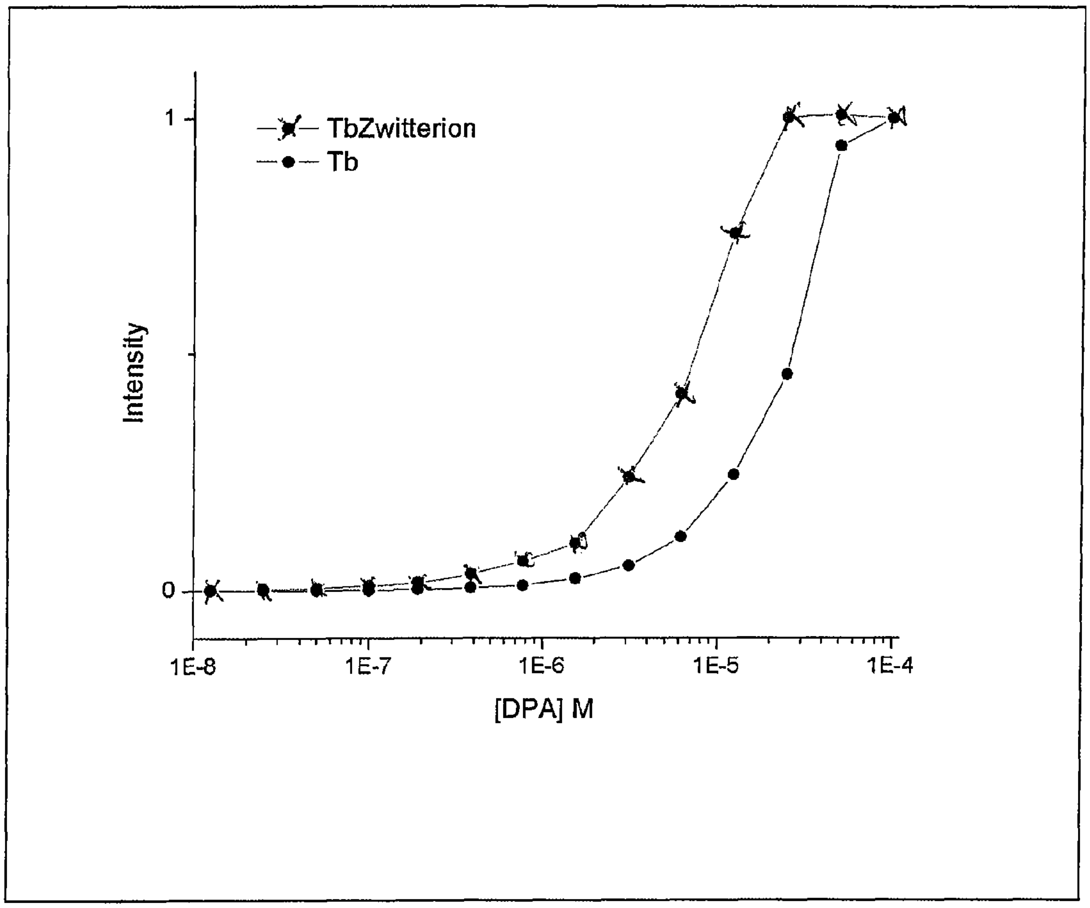
FIG. 10 is a graph of the experimental data showing the enhanced intensity in detection of DPA (M) using the EZ molecule to complex with terbium (Tb).

FIG. 8*b* shows the luminescence spectra before and after the generation of aerosolized bacterial spores. Clearly, the signal-to-noise ratio of 10, one cycle after spore introduction, shows that we can detect aerosolized spores with a response time of about 15 minutes. Spore lysing methods, such as sonication with microbeads, that do not require high temperature will lead to increased sampling rates.

Thus, we have demonstrated quantification of aerosolized bacterial spores with a response time of about 15 minutes or less, a sensitivity of $10^5$ spores/ml, and a dynamic range of four orders of magnitude. The sensitivity can be improved by optimizing aerosol collection and spectrometer performance. Ultimately, the most attractive feature we have demonstrated is the unattended monitoring of aerosolized bacterial spores for the duration of a workday (i.e. ~8 hrs).

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for anyone of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conception ally equivalent, what can be obviously substituted and also what essentially incorporates the essential idea of the invention.

We claim:

1. A method for live/dead assay for bacterial spores in a specimen, the method comprising:

providing a first positively charged multidentate ligand lanthanide complex in a predetermined amount of a first sample from the specimen of live and dead bacterial spores;

releasing Dipicolinic Acid (DPA) from the live bacterial spores by germination in the first sample;

combining the positively charged multidentate ligand lanthanide complex with the DPA released from the bacterial spores in the predetermined amount of the first sample;

exciting the combined positively charged multidentate ligand lanthanide complex and DPA released from the live bacterial spores to generate a first luminescence characteristic of the combined positively charged multidentate ligand lanthanide complex and DPA to detect a number of live bacterial spores in the first sample;

providing a second positively charged multidentate ligand lanthanide complex in predetermined amount of a second sample from the specimen of live and dead bacterial spores;

releasing DPA from the second sample of bacterial spores by autoclaving, sonication or microwaving;

combining the positively charged multidentate ligand lanthanide complex with the DPA released from the bacterial spores in the second predetermined amount of the second sample;

exciting the combined positively charged multidentate ligand lanthanide complex and DPA released from the bacterial spores to generate a second luminescence characteristic of the combined positively charged multidentate ligand lanthanide complex and DPA to detect a number of total bacterial spores in the second sample, said exciting comprising radiating the combined positively charged multidentate ligand lanthanide complex and DPA with ultraviolet light;

determining a number of dead bacterial spores by subtracting the number of live bacterial spores from the number of total bacterial spores; and generating a ratio of the DPA released from the live bacterial spores in the first sample to the DPA released from the dead bacterial spores in the second sample to obtain a live:dead ratio for the specimen.

2. The method of claim 1, further comprising detecting the first luminescence after generating the first luminescence and detecting the second luminescence after generating the second luminescence.

3. The method of claim 1, wherein the germination is carried out with L-alanine.

4. The method of claim 1, wherein the sonication is carried out with microspheres.

5. The method of claim 1, wherein the bacterial spores are in solution.

6. The method of claim 1, further comprising detecting the first luminescence after generating the first luminescence with an electro-optical circuit; and detecting the second luminescence after generating the second luminescence with an electro-optical circuit.

7. The method of claim 1, further comprising detecting the first luminescence after generating the first luminescence with a spectrometer; and detecting the second luminescence after generating the second luminescence with a spectrometer.

8. The method of claim 1, further comprising detecting the first luminescence after generating the first luminescence with a fluorometer; and detecting the second luminescence after generating the second luminescence with fluorometer.

9. The method of claim 1, further comprising detecting the first luminescence after generating the first luminescence with a lifetime gated luminescence spectrometer.

10. The method of claim 1, further comprising detecting the first luminescence after generating the first luminescence with Active Pixel Sensor (APS); and detecting the second luminescence after generating the second luminescence with APS.

* * * * *

UNITED STATES PATENT AND TRADEMARK OFFICE

CERTIFICATE OF CORRECTION

PATENT NO. : 8,173,359 B2
APPLICATION NO. : 11/810005
DATED : May 8, 2012
INVENTOR(S) : Adrian Ponce et al.

It is certified that error appears in the above-identified patent and that said Letters Patent is hereby corrected as shown below:

In column 1, line 15, the following wording should appear:

STATEMENT REGARDING FEDERALLY SPONSORED RESEARCH OR DEVELOPMENT

The invention described herein was made in the performance of work under a NASA contract, and is subject to the provisions of Public Law 96-517 (35 USC 202) in which the Contractor has elected to retain title.

Signed and Sealed this
Twenty-sixth Day of June, 2012

David J. Kappos
*Director of the United States Patent and Trademark Office*